US012637415B2

(12) United States Patent
Dykstra et al.

(10) Patent No.: US 12,637,415 B2
(45) Date of Patent: May 26, 2026

(54) LYOPHILIZED COMPOSITION COMPRISING (S)-ISOPROPYL 2-((S)-2-ACETAMIDO-3-(1H-INDOL-3-YL)PROPANAMIDO)-6-DIAZO-5-OXOHEXANOATE FOR INTRAVENOUS ADMINISTRATION AND THE USE THEREOF

(71) Applicant: DRACEN PHARMACEUTICALS, INC., Washington, DC (US)

(72) Inventors: Steven Dykstra, Apex, NC (US); Gary Elliott, Windsor, CO (US); Thomas M. Estok, Lakewood Ranch, FL (US); Stuart R. Gallant, Belmont, MA (US); Robert Christian Wild, Murrieta, CA (US); Jianmin Xu, San Diego, CA (US); Henry Acken Havel, Indianapolis, IN (US)

(73) Assignee: DRACEN PHARMACEUTICALS, INC., Washington, DC (US)

( * ) Notice: Subject to any disclaimer, the term of this patent is extended or adjusted under 35 U.S.C. 154(b) by 1079 days.

(21) Appl. No.: 17/765,483

(22) PCT Filed: Oct. 2, 2020

(86) PCT No.: PCT/US2020/054071

§ 371 (c)(1),
(2) Date: Mar. 31, 2022

(87) PCT Pub. No.: WO2021/067807

PCT Pub. Date: Apr. 8, 2021

(65) Prior Publication Data

US 2022/0332676 A1 Oct. 20, 2022

Related U.S. Application Data

(60) Provisional application No. 62/910,051, filed on Oct. 3, 2019.

(51) Int. Cl.

| | |
|---|---|
| ***C07C 245/18*** | (2006.01) |
| ***A61K 9/00*** | (2006.01) |
| ***A61K 31/4172*** | (2006.01) |
| ***C08F 26/10*** | (2006.01) |

(52) U.S. Cl.

CPC .......... *C07C 245/18* (2013.01); *A61K 9/0021* (2013.01); *A61K 31/4172* (2013.01); *C08F 26/10* (2013.01)

(58) Field of Classification Search

CPC C07C 245/18; A61K 9/0021; A61K 31/4172; C08F 26/10

See application file for complete search history.

(56) References Cited

U.S. PATENT DOCUMENTS

| | | | |
|---|---|---|---|
| 10,336,778 | B2 | 7/2019 | Slusher et al. |
| 10,568,868 | B2 | 2/2020 | Slusher et al. |
| 10,738,066 | B2 | 8/2020 | Slusher et al. |
| 10,842,763 | B2 | 11/2020 | Slusher et al. |
| 10,954,257 | B2 | 3/2021 | Slusher et al. |
| 11,185,534 | B2 | 11/2021 | Slusher et al. |
| 2013/0289012 | A1 | 10/2013 | Gu et al. |
| 2018/0193362 | A1 | 7/2018 | Slusher et al. |
| 2018/0222930 | A1 | 8/2018 | Slusher et al. |
| 2021/0145779 | A1 | 5/2021 | Slusher et al. |
| 2021/0206787 | A1 | 7/2021 | Slusher et al. |
| 2022/0089522 | A1 | 3/2022 | Lawson et al. |
| 2022/0194898 | A1 | 6/2022 | Lawson et al. |
| 2023/0009398 | A1 | 1/2023 | Slusher et al. |

FOREIGN PATENT DOCUMENTS

| | | | |
|---|---|---|---|
| WO | WO-2020150639 | A1 | 7/2020 |
| WO | WO-2022072820 | A1 | 4/2022 |

OTHER PUBLICATIONS

Challener "For Lyophilization, Excipients Really Do Matter" BioPharm International, Jan. 2017, p. 32-35 (Year: 2017).*

Ahluwalia., G. S., et.al., "Metabolism and Action of Amino Acid Analog Anti-cancer Agents," Pharmacology & Therapeutics 46(2):243-271, Pergamon Press, United Kingdom (1990).

(Continued)

*Primary Examiner* — Matthew P Coughlin
*Assistant Examiner* — Jalisa Holmes Ferguson
(74) *Attorney, Agent, or Firm* — STERNE, KESSLER, GOLDSTEIN & FOX P.L.L.C.

(57) ABSTRACT

The present disclosure provides lyophilates comprising (S)-isopropyl 2-((S)-2-acetamido-3-(1H-indol-3-yl)propanamido)-6-diazo-5-oxohexanoate: and pharmaceutical compositions, pharmaceutical formulations, and uses thereof.

(I)

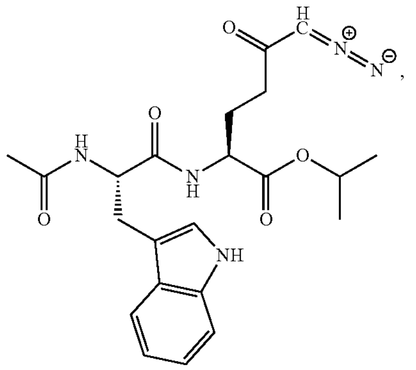

17 Claims, No Drawings

(56) References Cited

OTHER PUBLICATIONS

International Search Report and Written Opinion for International Application No. PCT/US2020/054071, ISA/US, Commissioner for Patents, Alexandria, Virginia, mailed Jan. 13, 2021, 8 pages.
Kasper, J. C., et al., "Development of a lyophilized plasmid/LPEI polyplex formulation with long-term stability—A step closer from promising technology to application," Journal of Controlled Release 151(3):246-255, Elsevier, Netherlands (May 2011).
Lynch, G., et al., "Phase II evaluation of DON (6-diazo-5-oxo-L-norleucine) in patients with advanced colorectal carcinoma," American Journal of Clinical Oncology 5(5):541-543, Lippincott Williams & Wilkins, United States (Oct. 1982).
Rosenfeld, H. and Roberts, J., "Enhancement of antitumor activity of glutamine antagonists 6-diazo-5-oxo-L-norleucine and acivicin in cell culture by glutaminase-asparaginase," Cancer Research 41(4):1324-1328, American Association for Cancer Research, United States (Apr. 1981).

* cited by examiner

LYOPHILIZED COMPOSITION COMPRISING (S)-ISOPROPYL 2-((S)-2-ACETAMIDO-3-(1H-INDOL-3-YL)PROPANAMIDO)-6-DIAZO-5-OXOHEXANOATE FOR INTRAVENOUS ADMINISTRATION AND THE USE THEREOF

BACKGROUND OF THE INVENTION

6-Diazo-5-oxo-L-norleucine (DON) is a glutamine antagonist that exhibits promising activity in preclinical models to treat a variety of diseases such as cancer. See, e.g., Ahluwalia et al., *Pharmac The.* 46:243-371 (1990). But the clinical development of DON has been hampered by its dose-limiting toxicity in humans, especially in the intestinal epithelium. See, e.g., Rosenfeld and Roberts, *Cancer Research* 41:1324-1328 (1981) and Lynch et al., *Am J Clin Oncol* (*CCT*) 5:541-543 (1982). Administering DON as a prodrug may help mitigate this toxicity.

U.S. Pat. No. 10,336,778 B2 discloses (S)-isopropyl 2-((S)-2-acetamido-3-(1H-indol-3-yl)propanamido)-6-diazo-5-oxohexanoate ("Compound 1") and other prodrugs of DON for the treatment of cancer and other diseases. There exists a need for pharmaceutical compositions comprising Compound 1 for intravenous administration to subject.

BRIEF SUMMARY OF THE INVENTION

In one aspect, the disclosure provides a lyophilate comprising Compound 1.

In another aspect, the disclosure provides a lyophilate comprising Compound 1, and a stabilizing agent, e.g., polyvinylpyrrolidone.

In another aspect, the disclosure provides a lyophilate comprising Compound 1, and a buffering agent, e.g., L-histidine.

In another aspect, the disclosure provides a lyophilate comprising Compound 1, a stabilizing agent, and a buffering agent.

In another aspect, the disclosure provides a pharmaceutical composition comprising a lyophilate comprising Compound 1 that has been reconstituted in a solvent, e.g., water and ethanol.

In another aspect, the disclosure provides a pharmaceutical formulation comprising a lyophilate comprising Compound 1 for intravenous administration to a subject.

In another aspect, the disclosure provides a method for treating a cancer in a subject in need thereof comprising administering a therapeutically effective amount of a pharmaceutical formulation comprising a lyophilate comprising Compound 1 to a subject in need thereof.

In another aspect, the disclosure provides a method of making the lyophilate comprising Compound 1.

In another aspect, the disclosure provides a method of making the pharmaceutical composition comprising a lyophilate comprising Compound 1.

In another aspect, the disclosure provides a method of making the pharmaceutical formulation comprising a lyophilate comprising Compound 1.

In another aspect, the disclosure provides a kit comprising the lyophilate comprising Compound 1 packaged as single unit dose in a vial.

DETAILED DESCRIPTION OF THE INVENTION

I. Lyophilates of the Disclosure

In one embodiment, the disclosure provides a lyophilate comprising Compound 1.

In another embodiment, the disclosure provides a lyophilate comprising Compound 1 and a stabilizing agent. In another embodiment, the Compound 1/stabilizing agent weight ratio is about 10 to about 0.1. In another embodiment, the Compound 1/stabilizing agent weight ratio is about 5 to about 0.5. In another embodiment, the Compound 1/stabilizing agent weight ratio is about 5 to about 0.25. In another embodiment, the Compound 1/stabilizing agent weight ratio is about 1. In another embodiment, the Compound 1/stabilizing agent weight ratio is about 0.9. In another embodiment, the Compound 1/stabilizing agent weight ratio is about 0.8. In another embodiment, the Compound 1/stabilizing agent weight ratio is about 0.7. In another embodiment, the Compound 1/stabilizing agent weight ratio is about 0.67. In another embodiment, the Compound 1/stabilizing agent weight ratio is about 0.6. In another embodiment, the Compound 1/stabilizing agent weight ratio is about 0.5. In another embodiment, the stabilizing agent is polyvinylpyrrolidone.

In another embodiment, the disclosure provides a lyophilate comprising Compound 1 and a buffering agent. In another embodiment, the Compound 1/buffering agent weight ratio is about 20 to about 0.5. In another embodiment, the Compound 1/buffering agent weight ratio is about 20 to about 1. In another embodiment, the Compound 1/buffering agent weight ratio is about 15 to about 5. In another embodiment, the Compound 1/buffering agent weight ratio is about 15 to about 2. In another embodiment, the Compound 1/buffering agent weight ratio is about 10. In another embodiment, the Compound 1/buffering agent weight ratio is about 9. In another embodiment, the Compound 1/buffering agent weight ratio is about 8. In another embodiment, the Compound 1/buffering agent weight ratio is about 7. In another embodiment, the Compound 1/buffering agent weight ratio is about 6.5. In another embodiment, the Compound 1/buffering agent weight ratio is about 6. In another embodiment, the Compound 1/buffering agent weight ratio is about 5. In another embodiment, the Compound 1/buffering agent weight ratio is about 4. In another embodiment, the buffering agent is L-histidine.

In another embodiment, the disclosure provides a lyophilate comprising Compound 1, a stabilizing agent, and a buffering agent.

In another embodiment, the disclosure provides a lyophilate comprising about 10 mg to about 110 mg of Compound 1. In another embodiment, the disclosure provides a lyophilate comprising about 20 mg to about 100 mg of Compound 1. In another embodiment, the disclosure provides a lyophilate comprising about 30 mg to about 90 mg of Compound 1. In another embodiment, the disclosure provides a lyophilate comprising about 40 mg to about 80 mg of Compound 1. In another embodiment, the disclosure provides a lyophilate comprising about 40 mg to about 50 mg of Compound 1. In another embodiment, the disclosure provides a lyophilate comprising about 40 mg to about 45 mg of Compound 1. In another embodiment, the disclosure provides a lyophilate comprising about 10 mg, about 15 mg, about 20 mg, about 25 mg, about 30 mg, about 35 mg, about 40 mg, about 42 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, or about 110 mg of Compound 1.

In another embodiment, the disclosure provides a lyophilate comprising about 10 mg to about 110 mg of a stabilizing agent. In another embodiment, the disclosure provides a lyophilate comprising about 20 mg to about 100 mg of a stabilizing agent. In another embodiment, the disclosure provides a lyophilate comprising about 30 mg to about 90 mg of a stabilizing agent. In another embodiment, the disclosure provides a lyophilate comprising about 40 mg to about 80 mg of a stabilizing agent. In another embodiment, the disclosure provides a lyophilate comprising about 50 mg to about 70 mg of a stabilizing agent. In another embodiment, the disclosure provides a lyophilate comprising about 60 mg to about 65 mg of a stabilizing agent. In another embodiment, the disclosure provides a lyophilate comprising about 10 mg, about 15 mg, about 20 mg, about 25 mg, about 30 mg, about 35 mg, about 40 mg, about 42 mg, about 45 mg, about 50 mg, about 55 mg, about 60 mg, about 63, about 65 mg, about 70 mg, about 75 mg, about 80 mg, about 85 mg, about 90 mg, about 95 mg, about 100 mg, about 105 mg, or about 110 mg of a stabilizing agent.

In another embodiment, the disclosure provides a lyophilate comprising about 0.1 mg to about 15 mg of a buffering agent. In another embodiment, the disclosure provides a lyophilate comprising about 0.5 mg to about 12 mg of a buffering agent. In another embodiment, the disclosure provides a lyophilate comprising about 1 mg to about 10 mg of a buffering agent. In another embodiment, the disclosure provides a lyophilate comprising about 3 mg to about 8 mg of a buffering agent. In another embodiment, the disclosure provides a lyophilate comprising about 5 mg to about 7 mg of a buffering agent. In another embodiment, the disclosure provides a lyophilate comprising about 5.5 mg to about 6.5 mg of a buffering agent. In another embodiment, the disclosure provides a lyophilate comprising about 0.1 mg, about 0.5 mg, about 1 mg, about 1.5 mg, about 2 mg, about 2.5 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg, about 10 mg, about 10.5 mg, about 11 mg, about 11.5 mg, about 12 mg, about 12.5 mg, about 13 mg, about 13.5 mg, about 14 mg, about 14.5 mg, or about 15 mg of a buffering agent.

In another embodiment, the disclosure provides a lyophilate comprising about 63 mg of Compound 1, about 63 mg of polyvinylpyrrolidone (PVP), and about 6.5 mg of L-histidine.

In another embodiment, the disclosure provides a lyophilate consisting essentially of about 63 mg of Compound 1, about 63 mg of polyvinylpyrrolidone (PVP), and about 6.5 mg of L-histidine.

In another embodiment, the disclosure provides a lyophilate consisting of about 63 mg of Compound 1, about 63 mg of polyvinylpyrrolidone (PVP), and about 6.5 mg of L-histidine.

In another embodiment, the disclosure provides a lyophilate comprising about 42 mg of Compound 1, about 63 mg of polyvinylpyrrolidone (PVP), and about 6.5 mg of L-histidine.

In another embodiment, the disclosure provides a lyophilate consisting essentially of about 42 mg of Compound 1, about 63 mg of polyvinylpyrrolidone (PVP), and about 6.5 mg of L-histidine.

In another embodiment, the disclosure provides a lyophilate consisting of about 42 mg of Compound 1, about 63 mg of polyvinylpyrrolidone (PVP), and about 6.5 mg of L-histidine.

In another embodiment, the moisture content of the lyophilate is about 4% or less as determined by the Karl Fischer method. In another embodiment, the moisture content of the lyophilate is about 3% or less. In another embodiment, the moisture content of the lyophilate is about 2% or less. In another embodiment, the moisture content of the lyophilate is about 1% or less. In another embodiment, the moisture content of the lyophilate is about 0.9%. In another embodiment, the moisture content of the lyophilate is about 0.8%. In another embodiment, the moisture content of the lyophilate is about 0.7%. In another embodiment, the moisture content of the lyophilate is about 0.6%. In another embodiment, the moisture content of the lyophilate is about 0.5%. In another embodiment, the moisture content of the lyophilate is about 0.4%. In another embodiment, the moisture content of the lyophilate is about 0.3%. In another embodiment, the moisture content of the lyophilate is about 0.2%. In another embodiment, the moisture content of the lyophilate is about 0.1%.

In another embodiment, the chemical purity of Compound 1 in the lyophilate is about 96% to about 99.9% as measured by HPLC. In another embodiment, the chemical purity of Compound 1 in the lyophilate is about 96%. In another embodiment, the chemical purity of Compound 1 in the lyophilate is about 96.5%. In another embodiment, the chemical purity of Compound 1 in the lyophilate is about 97%. In another embodiment, the chemical purity of Compound 1 in the lyophilate is about 97.5%. In another embodiment, the chemical purity of Compound 1 in the lyophilate is about 98%. In another embodiment, the chemical purity of Compound 1 in the lyophilate is about 98.5%. In another embodiment, the chemical purity of Compound 1 in the lyophilate is about 99.0%. In another embodiment, the chemical purity of Compound 1 in the lyophilate is about 99.5%.

The lyophilates described in this section are collectively referred to as a "Lyophilate of the Disclosure."

II. Pharmaceutical Compositions of the Disclosure

In another embodiment, the disclosure provides a pharmaceutical composition comprising a Lyophilate of the Disclosure dissolved, i.e., reconstituted, in a solvent.

In one embodiment, the solvent comprises water, e.g., Sterile Water for Injection, USP.

In another embodiment, the solvent comprises water and ethanol.

In another embodiment, the solvent comprises about 40% to about 60% ethanol and about 40% to about 60% water.

In another embodiment, the solvent comprises about 55% to about 45% ethanol and about 45% to about 55% water.

In another embodiment, the solvent comprises about 70% to about 90% ethanol and about 10% to about 30% water.

In another embodiment, the solvent comprises about 75% to about 85% ethanol and about 15% to about 25% water.

In another embodiment, the solvent comprises about 40% ethanol and about 60% water. In another embodiment, the solvent comprises about 45% ethanol and about 55% water. In another embodiment, the solvent comprises about 50% ethanol and about 50% water. In another embodiment, the solvent comprises about 55% ethanol and about 45% water. In another embodiment, the solvent comprises about 60% ethanol and about 40% water. In another embodiment, the solvent comprises about 65% ethanol and about 35% water. In another embodiment, the solvent comprises about 70% ethanol and about 30% water. In another embodiment, the solvent comprises about 75% ethanol and about 25% water. In another embodiment, the solvent consists of about 80% ethanol and about 20% water. In another embodiment, the solvent comprises about 85% ethanol and about 15% water. In another embodiment, the solvent comprises about 90% ethanol and about 10% water.

In another embodiment, the disclosure provides a pharmaceutical composition comprising a Lyophilate of the Disclosure dissolved, i.e., reconstituted, in a solvent, wherein the concentration of Compound 1 is about 5 mg/mL to about 25 mg/mL. In another embodiment, the concentration of Compound 1 is about 10 mg/mL to about 20 mg/mL. In another embodiment, the concentration of Compound 1 is about 5 mg/mL to about 15 mg/mL. In another embodiment, the concentration of Compound 1 is about 5 mg/mL. In another embodiment, the concentration of Compound 1 is about 10 mg/mL. In another embodiment, the concentration of Compound 1 is about 15 mg/mL.

In another embodiment, the disclosure provides a pharmaceutical composition comprising about 63 mg of Compound 1, about 63 mg of polyvinylpyrrolidone (PVP), about 6.5 mg of L-histidine, and about 4.2 mL of a solvent, e.g., about 2.1 mL ethanol and about 2.1 mL WFI.

In another embodiment, the disclosure provides a pharmaceutical composition comprising about 42 mg of Compound 1, about 63 mg of polyvinylpyrrolidone (PVP), about 6.5 mg of L-histidine, and about 4.2 mL of a solvent, e.g., about 2.1 mL ethanol and about 2.1 mL WFI.

The pharmaceutical compositions described in this section are collectively referred to as a "Pharmaceutical Composition of the Disclosure."

III. Pharmaceutical Formulations of the Disclosure

In another embodiment, the disclosure provides a pharmaceutical formulation comprising a Pharmaceutical Composition of the Disclosure and a diluent.

In one embodiment, the diluent is normal saline. Other diluents may also be used including 5% dextrose, lactated Ringer's solution, or any other sterile fluid designed to be compatible with administration, e.g., by intravenous infusion, to humans.

In another embodiment, the disclosure provides a pharmaceutical formulation comprising a Pharmaceutical Composition of the Disclosure and a diluent, wherein the concentration of Compound 1 is about 0.005 to about 2.4 mg/mL. In another embodiment, the concentration of Compound 1 is about 0.012 to about 0.24 mg/mL. In another embodiment, the concentration of Compound 1 is about 0.05 to about 1.2 mg/mL. In another embodiment, the concentration of Compound 1 is about 0.1 to about 0.6 mg/mL. In another embodiment, the concentration of Compound 1 is about 0.012 mg/mL. In another embodiment, the concentration of Compound 1 is about 0.24 mg/mL. In another embodiment, the concentration of Compound 1 is about 0.3 mg/mL.

The pharmaceutical compositions described in this section are collectively referred to as a "Pharmaceutical Formulation of the Disclosure."

IV. Therapeutic Methods

In another embodiment, the disclosure provides a method for treating cancer in a subject in need thereof comprising administering a therapeutically effective amount of a Pharmaceutical Formulation of the Disclosure to the subject.

In another embodiment, the disclosure provides a method for treating cancer in a subject in need thereof comprising administering a therapeutically effective amount of a Pharmaceutical Formulation of the Disclosure to the subject in combination with one or more optional therapeutic agents.

In another embodiment, the disclosure provides a Pharmaceutical Formulation of the Disclosure for use in treating cancer in a subject.

In another embodiment, the disclosure provides a Pharmaceutical Formulation of the Disclosure for use in treating cancer in a subject, wherein the Pharmaceutical Formulation of the Disclosure is to be administered in combination with one or more optional therapeutic agents.

In another embodiment, the Pharmaceutical Formulation of the Disclosure is administered intravenously to the subject.

In another embodiment, the Pharmaceutical Formulation of the Disclosure administered to the subject according to an intermittent dosing schedule. For example, the Pharmaceutical Formulation of the Disclosure may be administered to a subject three days a week on non-consecutive days, e.g., Monday-Wednesday-Friday.

In one embodiment, the cancer is a solid tumor.

In another embodiment, the cancer is a hematological cancer. In another embodiment, the hematological cancer is acute lymphocytic leukemia, chronic lymphocytic leukemia (including B-cell chronic lymphocytic leukemia), or acute myeloid leukemia.

In another embodiment, the cancer is any one or more of the cancers of Table 1.

TABLE 1

| | | | |
|---|---|---|---|
| adrenal cancer | acinic cell carcinoma | acoustic neuroma | acral lentigious melanoma |
| acrospiroma | acute eosinophilic leukemia | acute erythroid leukemia | acute lymphoblastic leukemia |
| acute megakaryoblastic leukemia | acute monocytic leukemia | acute promyelocytic leukemia | adenocarcinoma |
| adenoid cystic carcinoma | adenoma | adenomatoid odontogenic tumor | adenosquamous carcinoma |
| adipose tissue neoplasm | adrenocortical carcinoma | adult T-cell leukemia/lymphoma | aggressive NK-cell leukemia |
| AIDS-related lymphoma | alveolar rhabdomyosarcoma | alveolar soft part sarcoma | ameloblastic fibroma |
| anaplastic large cell lymphoma | anaplastic thyroid cancer | angioimmunoblastic T-cell lymphoma | angiomyolipoma |

TABLE 1-continued

| | | | |
|---|---|---|---|
| angiosarcoma | astrocytoma | atypical teratoid rhabdoid tumor | B-cell chronic lymphocytic leukemia |
| B-cell prolymphocytic leukemia | B-cell lymphoma | basal cell carcinoma | biliary tract cancer |
| bladder cancer | blast oma | bone cancer | Brenner tumor |
| Brown tumor | Burkitt's lymphoma | breast cancer | brain cancer |
| carcinoma | carcinoma in situ | carcinosarcoma | cartilage tumor |
| cementoma | myeloid sarcoma | chondroma | chordoma |
| choriocarcinoma | choroid plexus papilloma | clear-cell sarcoma of the kidney | craniopharyngioma |
| cutaneous T-cell lymphoma | cervical cancer | colorectal cancer | Degos disease |
| desmoplastic small round cell tumor | diffuse large B-cell lymphoma | dysembryoplastic neuroepithelial tumor | dysgerminoma |
| embryonal carcinoma | endocrine gland neoplasm | endodermal sinus tumor | enteropathy-associated T-cell lymphoma |
| esophageal cancer | fetus in fetu | fibroma | fibrosarcoma |
| follicular lymphoma | follicular thyroid cancer | ganglioneuroma | gastrointestinal cancer |
| germ cell tumor | gestational choriocarcinoma | giant cell fibroblastoma | giant cell tumor of the bone |
| glial tumor | glioblastoma multiforme | glioma | gliomatosis cerebri |
| glucagonoma | gonadoblastoma | granulosa cell tumor | gynandroblastoma |
| gallbladder cancer | gastric cancer | hairy cell leukemia | hemangioblastoma |
| head and neck cancer | hemangiopericytoma | hematological cancer | hepatoblastoma |
| hepatosplenic T-cell lymphoma | Hodgkin's lymphoma | non-Hodgkin's lymphoma | invasive lobular carcinoma |
| intestinal cancer | kidney cancer | laryngeal cancer | lentigo maligna |
| lethal midline carcinoma | leukemia | leydig cell tumor | liposarcoma |
| lung cancer | lymphangioma | lymphangiosarcoma | lymphoepithelioma |
| lymphoma | acute lymphocytic leukemia | acute myelogeous leukemia | chronic lymphocytic leukemia |
| liver cancer | small cell lung cancer | non-small cell lung cancer | MALT lymphoma |
| malignant fibrous histiocytoma | malignant peripheral nerve sheath tumor | malignant triton tumor | mantle cell lymphoma |
| marginal zone B-cell lymphoma | mast cell leukemia | mediastinal germ cell tumor | medullary carcinoma of the breast |
| medullary thyroid cancer | medulloblastoma | melanoma | meningioma |
| merkel cell cancer | mesothelioma | metastatic urothelial carcinoma | mixed Mullerian tumor |
| mucinous tumor | multiple myeloma | muscle tissue neoplasm | mycosis fungoides |
| myxoid liposarcoma | myxoma | myxosarcoma | nasopharyngeal carcinoma |
| neurinoma | neuroblastoma | neurofibroma | neuroma |
| nodular melanoma | ocular cancer | oligoastrocytoma | oligodendroglioma |
| oncocytoma | optic nerve sheath meningioma | optic nerve tumor | oral cancer |
| osteosarcoma | ovarian cancer | Pancoast tumor | papillary thyroid cancer |
| paraganglioma | pinealoblastoma | pineocytoma | pituicytoma |
| pituitary adenoma | pituitary tumor | plasmacytoma | polyembryoma |
| precursor T-lymphoblastic lymphoma | primary central nervous system lymphoma | primary effusion lymphoma | preimary peritoneal cancer |
| prostate cancer | pancreatic cancer | pharyngeal cancer | pseudomyxoma periotonei |
| renal cell carcinoma | renal medullary carcinoma | retinoblastoma | rhabdomyoma |
| rhabdomyosarcoma | Richter's transformation | rectal cancer | sarcoma |
| Schwannomatosis | seminoma | Sertoli cell tumor | sex cord-gonadal stromal tumor |
| signet ring cell carcinoma | skin cancer | small blue round cell tumors | small cell carcinoma |
| soft tissue sarcoma | somatostatinoma | soot wart | spinal tumor |
| splenic marginal zone lymphoma | squamous cell carcinoma | synovial sarcoma | Sezary's disease |
| small intestine cancer | squamous carcinoma | stomach cancer | T-cell lymphoma |

TABLE 1-continued

| | | | |
|---|---|---|---|
| testicular cancer | thecoma | thyroid cancer | transitional cell carcinoma |
| throat cancer | urachal cancer | urogenital cancer | urothelial carcinoma |
| uveal melanoma | uterine cancer | verrucous carcinoma | visual pathway glioma |
| vulvar cancer | vaginal cancer | Waldenstrom's macroglobulinemia | Warthin's tumor |
| Wilms' tumor | | | |

In another embodiment, the cancer is any one or more of the cancers of Table 2.

TABLE 2

| | |
|---|---|
| acute lymphocytic leukemia (ALL) | acute eosinophilic leukemia |
| acute myeloid leukemia (AML) | acute erythroid leukemia |
| chronic lymphocytic leukemia (CLL) | acute lymphoblastic leukemia |
| small lymphocytic lymphoma (SLL) | acute megakaryoblastic leukemia |
| multiple myeloma (MM) | acute monocytic leukemia |
| Hodgkins lymphoma (HL) | acute promyelocytic leukemia |
| non-Hodgkin's lymphoma (NHL) | acute myelogeous leukemia |
| mantle cell lymphoma (MCL) | B-cell prolymphocytic leukemia |
| marginal zone B-cell lymphoma | B-cell lymphoma |
| splenic marginal zone lymphoma | MALT lymphoma |
| follicular lymphoma (FL) | precursor T-lymphoblastic lymphoma |
| Waldenstrom's macroglobulinemia (WM) | T-cell lymphoma |
| diffuse large B-cell lymphoma (DLBCL) | mast cell leukemia |
| marginal zone lymphoma (MZL) | adult T cell leukemia/lymphoma |
| hairy cell leukemia (HCL) | aggressive NK-cell leukemia |
| Burkitt's lymphoma (BL) | angioimmunoblastic T-cell lymphoma |
| Richter's transformation | |

In another embodiment, the cancer is selected from the group consisting of squamous cell carcinoma of the head and neck, adenocarcinoma squamous cell carcinoma of the esophagus, adenocarcinoma of the stomach, adenocarcinoma of the colon, hepatocellular carcinoma, cholangiocarcinoma of the biliary system, adenocarcinoma of gall bladder, adenocarcinoma of the pancreas, ductal carcinoma in situ of the breast, adenocarcinoma of the breast, adenocarcinoma of the lungs, squamous cell carcinoma of the lungs, transitional cell carcinoma of the bladder, squamous cell carcinoma of the bladder, squamous cell carcinoma of the cervix, adenocarcinoma of the cervix, endometrial carcinoma, penile squamous cell carcinoma, and squamous cell carcinoma of the skin.

In another embodiment, a precancerous tumor is selected from the group consisting of leukoplakia of the head and neck, Barrett's esophagus, metaplasia of the stomach, adenoma of the colon, chronic hepatitis, bile duct hyperplasia, pancreatic intraepithelial neoplasia, atypical adenomatous hyperplasia of the lungs, dysplasia of the bladder, cervical initraepithelial neoplasia, penile intraepithelial neoplasia, and actinic keratosis of the skin.

In another embodiment, the cancer is selected from the group consisting of hepatocellular carcinoma, glioblastoma, lung cancer, breast cancer, head and neck cancer, prostate cancer, melanoma, and colorectal cancer.

In another embodiment, the cancer is selected from the group consisting of colorectal cancer, breast cancer, lymphoma, melanoma, kidney cancer, and lung cancer.

In another embodiment, the cancer has become resistant to conventional cancer treatments. The term "conventional cancer treatments" as used herein refers to any cancer drugs, biologics, or radiotherapy, or combination of cancer drugs and/or biologics and/or radiotherapy that have been tested and/or approved for therapeutic use in humans by the U.S. Food and Drug Administration, European Medicines Agency, or similar regulatory agency.

V. Optional Therapeutic Agents

In some therapeutic methods and uses of the disclosure, a Pharmaceutical Formulation of the Disclosure is administered to a subject having cancer as a single agent. In other therapeutic methods and uses of the disclosure, a Pharmaceutical Formulation of the Disclosure is administered to a subject having cancer in combination with one or more optional therapeutic agents. In one embodiment, a Pharmaceutical Formulation of the Disclosure is administered in combination with one optional therapeutic agent. In another embodiment, a Pharmaceutical Formulation of the Disclosure is administered in combination with two optional therapeutic agents. In another embodiment, a Pharmaceutical Formulation of the Disclosure is administered in combination with three optional therapeutic agents. Optional therapeutic agents useful in treating cancer patients include those known in the art as well as those developed in the future.

Optional therapeutic agents are administered in an amount to provide their desired therapeutic effect. The effective dosage range for each optional therapeutic agent is known in the art, and the optional therapeutic agent is administered to an individual in need thereof within such established ranges.

A Pharmaceutical Formulation of the Disclosure and the optional therapeutic agent(s) can be administered separately as multi-unit doses in any order, e.g., wherein a Pharmaceutical Formulation of the Disclosure is administered before the optional therapeutic agent(s), or vice versa. One or more doses of a Pharmaceutical Formulation of the Disclosure and the optional therapeutic agent(s) can be administered to the subject.

In one embodiment, the optional therapeutic agent is an immune checkpoint inhibitor. Examples of immune checkpoint inhibitors include PD-1 inhibitors, PD-L1 inhibitors, CTLA-4 inhibitors, LAG3 inhibitors, TIM3 inhibitors, cd47 inhibitors, TIGIT inhibitors, and B7-H1 inhibitors. Thus, in one embodiment, the immune checkpoint inhibitor is selected from the group consisting of a PD-1 inhibitor, a PD-L1 inhibitor, a CTLA-4 inhibitor, a LAG3 inhibitor, a TIM3 inhibitor, and a cd47 inhibitor.

In another embodiment, the immune checkpoint inhibitor is a programmed cell death (PD-1) inhibitor. PD-1 is a T-cell coinhibitory receptor that plays a pivotal role in the ability of tumor cells to evade the host's immune system. Blockage of interactions between PD-1 and PD-L1, a ligand of PD-1, enhances immune function and mediates antitumor activity. Examples of PD-1 inhibitors include antibodies that specifically bind to PD-1. Particular anti-PD-1 antibodies include, but are not limited to nivolumab, pembrolizumab, STI-A1014, pidilzumab, and cemiplimab-rwlc. For a general discussion of the availability, methods of production, mechanism of action, and clinical studies of anti-PD-1 antibodies, see U.S. 2013/0309250, U.S. Pat. Nos. 6,808,710, 7,595,048, 8,008,449, 8,728,474, 8,779,105, 8,952,136, 8,900,587, 9,073,994, 9,084,776, and Naido et al., *British Journal of Cancer* 111:2214-19 (2014).

In another embodiment, the immune checkpoint inhibitor is a PD-L1 (also known as B7-H1 or CD274) inhibitor. Examples of PD-L1 inhibitors include antibodies that specifically bind to PD-L1. Particular anti-PD-L1 antibodies include, but are not limited to, avelumab, atezolizumab, durvalumab, and BMS-936559. For a general discussion of the availability, methods of production, mechanism of action, and clinical studies, see U.S. Pat. No. 8,217,149, U.S. 2014/0341917, U.S. 2013/0071403, WO 2015036499, and Naido et al., *British Journal of Cancer* 111:2214-19 (2014).

In another embodiment, the immune checkpoint inhibitor is a CTLA-4 inhibitor. CTLA-4, also known as cytotoxic T-lymphocyte antigen 4, is a protein receptor that downregulates the immune system. CTLA-4 is characterized as a "brake" that binds costimulatory molecules on antigen-presenting cells, which prevents interaction with CD28 on T cells and also generates an overtly inhibitory signal that constrains T cell activation. Examples of CTLA-4 inhibitors include antibodies that specifically bind to CTLA-4. Particular anti-CTLA-4 antibodies include, but are not limited to, ipilimumab and tremelimumab. For a general discussion of the availability, methods of production, mechanism of action, and clinical studies, see U.S. Pat. Nos. 6,984,720, 6,207,156, and Naido et al., *British Journal of Cancer* 111:2214-19 (2014).

In another embodiment, the immune checkpoint inhibitor is a LAG3 inhibitor. LAG3, Lymphocyte Activation Gene 3, is a negative co-stimulatory receptor that modulates T cell homeostatis, proliferation, and activation. In addition, LAG3 has been reported to participate in regulatory T cells (Tregs) suppressive function. A large proportion of LAG3 molecules are retained in the cell close to the microtubule-organizing center, and only induced following antigen specific T cell activation. U.S. 2014/0286935. Examples of LAG3 inhibitors include antibodies that specifically bind to LAG3. Particular anti-LAG3 antibodies include, but are not limited to, GSK2831781. For a general discussion of the availability, methods of production, mechanism of action, and studies, see, U.S. 2011/0150892, U.S. 2014/0093511, U.S. 20150259420, and Huang et al., *Immunity* 21:503-13 (2004).

In another embodiment, the immune checkpoint inhibitor is a TIM3 inhibitor. TIM3, T-cell immunoglobulin and mucin domain 3, is an immune checkpoint receptor that functions to limit the duration and magnitude of $T_H1$ and $T_C1$ T-cell responses. The TIM3 pathway is considered a target for anticancer immunotherapy due to its expression on dysfunctional $CD8^+$ T cells and Tregs, which are two reported immune cell populations that constitute immunosuppression in tumor tissue. Anderson, *Cancer Immunology Research* 2:393-98 (2014). Examples of TIM3 inhibitors include antibodies that specifically bind to TIM3. For a general discussion of the availability, methods of production, mechanism of action, and studies of TIM3 inhibitors, see U.S. 20150225457, U.S. 20130022623, U.S. Pat. No. 8,522,156, Ngiow et al., *Cancer Res* 71: 6567-71 (2011), Ngiow, et al., *Cancer Res* 71:3540-51 (2011), and *Anderson, Cancer Immunology Res* 2:393-98 (2014).

In another embodiment, the immune checkpoint inhibitor is a cd47 inhibitor. See Unanue, *PNAS* 110:10886-87 (2013).

In another embodiment, the immune checkpoint inhibitor is a TIGIT inhibitor. See Harjunpää 1 and Guillerey, *Clin Exp Immunol* 200:108-119 (2019).

The term "antibody" is meant to include intact monoclonal antibodies, polyclonal antibodies, multispecific antibodies formed from at least two intact antibodies, and antibody fragments, so long as they exhibit the desired biological activity. In another embodiment, "antibody" is meant to include soluble receptors that do not possess the Fc portion of the antibody. In one embodiment, the antibodies are humanized monoclonal antibodies and fragments thereof made by means of recombinant genetic engineering.

Another class of immune checkpoint inhibitors include polypeptides that bind to and block PD-1 receptors on T-cells without triggering inhibitor signal transduction. Such peptides include B7-DC polypeptides, B7-H1 polypeptides, B7-1 polypeptides and B7-2 polypeptides, and soluble fragments thereof, as disclosed in U.S. Pat. No. 8,114,845.

Another class of immune checkpoint inhibitors include compounds with peptide moieties that inhibit PD-1 signaling. Examples of such compounds are disclosed in U.S. Pat. No. 8,907,053.

Another class of immune checkpoint inhibitors include inhibitors of certain metabolic enzymes, such as indoleamine 2,3 dioxygenase (IDO), which is expressed by infiltrating myeloid cells and tumor cells, and isocitrate dehydrogenase (IDH), which is mutated in leukemia cells. Mutants of the IDH enzyme lead to increased levels of 2-hydroxyglutarate (2-HG), which prevent myeloid differentiation. Stein et al., *Blood* 130:722-31 (2017); Wouters, *Blood* 130:693-94 (2017). Particular mutant IDH blocking agents include, but are not limited to, ivosidenib and enasidenib mesylate. Dalle and DiNardo, *Ther Adv Hematol* 9(7):163-73 (2018); Nassereddine et al., *Onco Targets Ther* 12:303-08 (2018). The IDO enzyme inhibits immune responses by depleting amino acids that are necessary for anabolic functions in T cells or through the synthesis of particular natural ligands for cytosolic receptors that are able to alter lymphocyte functions. Pardoll, *Nature Reviews. Cancer* 12:252-64 (2012); Löb, *Cancer Immunol Immunother* 58:153-57 (2009). Particular IDO blocking agents include, but are not limited to, levo-1-methyl typtophan (L-1MT) and 1-methyl-tryptophan (1MT). Qian et al., *Cancer Res* 69:5498-504 (2009); and Löb et al., *Cancer Immunol Immunother* 58:153-7 (2009).

In one embodiment, the immune checkpoint inhibitor is nivolumab, pembrolizumab, pidilizumab, STI-A1110, avelumab, atezolizumab, durvalumab, STI-A1014, ipilimumab, tremelimumab, GSK2831781, BMS-936559 or MED14736.

In another embodiment, the optional therapeutic agent is an epigenetic drug. As used herein, the term "epigenetic drug" refers to a therapeutic agent that targets an epigenetic regulator. Examples of epigenetic regulators include the histone lysine methyltransferases, histone arginine methyl transferases, histone demethylases, histone deacetylases, histone acetylases, and DNA methyltransferases. Histone deacetylase inhibitors include, but are not limited to, vorinostat and panobinostat lactate.

Additional examples of conventional therapies and anticancer agents that can be used in combination with a Pharmaceutical Formulation of the Disclosure include surgery, radiotherapy, e.g., gamma-radiation, neutron beam radiotherapy, electron beam radiotherapy, proton therapy, brachytherapy, and systemic radioactive isotopes, endocrine therapy, a biologic response modifier, e.g., an interferon, an interleukin, tumor necrosis factor (TNF), hyperthermia and cryotherapy, an agent to attenuate any adverse effect (e.g., an antiemetic), and any other approved biologic therapy or chemotherapy, e.g., a treatment regimen that uses drugs to stop the growth of cancer cells, either by killing the cells or by stopping them from dividing. Chemotherapy may be given by mouth, injection, or infusion, or on the skin, depending on the type and stage of the cancer being treated.

Nonlimiting exemplary antiproliferative compounds include an aromatase inhibitor; an anti-estrogen; an anti-androgen; a gonadorelin agonist; a topoisomerase I inhibitor; a topoisomerase II inhibitor; a microtubule active agent; an alkylating agent, e.g., temozolomide; a retinoid, a carontenoid, or a tocopherol; a cyclooxygenase inhibitor; an MMP inhibitor; an mTOR inhibitor; an antimetabolite; a platin compound; a methionine aminopeptidase inhibitor; a bisphosphonate; an antiproliferative antibody; a heparanase inhibitor; an inhibitor of Ras oncogenic isoforms; a telomerase inhibitor; a proteasome inhibitor; a compound used in the treatment of hematologic malignancies; a Flt-3 inhibitor; an Hsp90 inhibitor; a kinesin spindle protein inhibitor; a MEK inhibitor; an antitumor antibiotic; a nitrosourea; a compound targeting/decreasing protein or lipid kinase activity, a compound targeting/decreasing protein or lipid phosphatase activity, or any further anti-angiogenic compound.

Nonlimiting exemplary aromatase inhibitors include steroids, such as atamestane, exemestane, and formestane, and non-steroids, such as aminoglutethimide, roglethimide, pyridoglutethimide, trilostane, testolactone, ketokonazole, vorozole, fadrozole, anastrozole, and letrozole.

Nonlimiting anti-estrogens include tamoxifen, fulvestrant, raloxifene, and raloxifene hydrochloride. Anti-androgens include, but are not limited to, bicalutamide and apalutamide. Gonadorelin agonists include, but are not limited to, abarelix, goserelin, and goserelin acetate.

Nonlimiting exemplary topoisomerase I inhibitors include topotecan, gimatecan, irinotecan, camptothecin and its analogues, 9-nitrocamptothecin, and the macromolecular camptothecin conjugate PNU-166148. Topoisomerase II inhibitors include, but are not limited to, anthracyclines, such as doxorubicin, daunorubicin, epirubicin, idarubicin, and nemorubicin; anthraquinones, such as mitoxantrone and losoxantrone; and podophillotoxines, such as etoposide and teniposide.

Microtubule active agents include microtubule stabilizing, microtubule destabilizing compounds, and microtubulin polymerization inhibitors including, but not limited to, taxanes, such as paclitaxel and docetaxel; discodermolides; cochicine and epothilones and derivatives thereof.

Nonlimiting exemplary alkylating agents include cyclophosphamide, ifosfamide, melphalan, trabectedin, and nitrosoureas, such as carmustine and lomustine.

Nonlimiting exemplary matrix metalloproteinase inhibitors ("MMP inhibitors") include collagen peptidomimetic and nonpeptidomimetic inhibitors, tetracycline derivatives, batimastat, marimastat, prinomastat, metastat, BMS-279251, BAY 12-9566, TAA211, MMI270B, and AAJ996.

Nonlimiting exemplary mTOR inhibitors include compounds that inhibit the mammalian target of rapamycin (mTOR) and possess antiproliferative activity such as sirolimus, everolimus, CCI-779, and ABT578.

Nonlimiting exemplary antimetabolites include 5-fluorouracil (5-FU), capecitabine, gemcitabine, DNA demethylating compounds, such as 5-azacytidine and decitabine, methotrexate and edatrexate, and folic acid antagonists, such as pemetrexed.

Nonlimiting exemplary platin compounds include carboplatin, cis-platin, cisplatinum, and oxaliplatin.

Nonlimiting exemplary methionine aminopeptidase inhibitors include bengamide or a derivative thereof and PPI-2458.

Nonlimiting exemplary bisphosphonates include etridonic acid, clodronic acid, tiludronic acid, pamidronic acid, alendronic acid, ibandronic acid, risedronic acid, and zoledronic acid.

Nonlimiting exemplary heparanase inhibitors include compounds that target, decrease, or inhibit heparin sulfate degradation, such as PI-88 and OGT2115.

Nonlimiting exemplary compounds which target, decrease, or inhibit the oncogenic activity of Ras include farnesyl transferase inhibitors, such as L-744832, DK8G557, tipifarnib, and lonafarnib.

Nonlimiting exemplary telomerase inhibitors include compounds that target, decrease, or inhibit the activity of telomerase, such as compounds that inhibit the telomerase receptor, such as telomestatin.

Nonlimiting exemplary proteasome inhibitors include compounds that target, decrease, or inhibit the activity of the proteasome including, but not limited to, bortezomib. In some embodiments, the proteasome inhibitor is carfilzomib or ixazomib.

Nonlimiting exemplary FMS-like tyrosine kinase inhibitors, which are compounds targeting, decreasing or inhibiting the activity of FMS-like tyrosine kinase receptors (Flt-3R), include gilteritinib, interferon, I-β-D-arabinofuransylcytosine (ara-c), and bisulfan; and ALK inhibitors, which are compounds that target, decrease, or inhibit anaplastic lymphoma kinase, include alectinib, brigatinib, and lorlatinib.

Nonlimiting exemplary Flt-3 inhibitors include PKC412, midostaurin, a staurosporine derivative, SU11248, MLN518, and gilteritinib.

Nonlimiting exemplary HSP90 inhibitors include compounds targeting, decreasing, or inhibiting the intrinsic ATPase activity of HSP90; or degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins, or antibodies that inhibit the ATPase activity of HSP90, such as 17-allylamino,17-demethoxygeldanamycin (17AAG), a geldanamycin derivative; other geldanamycin related compounds; radicicol and HDAC inhibitors.

Nonlimiting exemplary protein tyrosine kinase and/or serine and/or threonine kinase inhibitors or lipid kinase inhibitors, include a) a compound targeting, decreasing, or inhibiting the activity of the platelet-derived growth factor-receptors (PDGFR), such as a compound that targets, decreases, or inhibits the activity of PDGFR, including olaratumab and N-phenyl-2-pyrimidine-amine derivatives, such as imatinib, SU1O1, SU6668, and GFB-111; b) a compound targeting, decreasing, or inhibiting the activity of the fibroblast growth factor-receptors (FGFR), such as erdafitinib and lenvatinib; c) a compound targeting, decreasing, or inhibiting the activity of the insulin-like growth factor receptor I (IGF-IR), such as brigatinib; d) a compound targeting, decreasing, or inhibiting the activity of the vascular endothelial growth factor-receptors (VEGFR), such as lenvatinib; e) a compound targeting, decreasing, or inhibiting the activity of the Trk receptor tyrosine kinase family, or ephrin B4 inhibitors, such as larotrectinib; f) a compound targeting, decreasing, or inhibiting the activity of the Axl receptor tyrosine kinase family; g) a compound targeting, decreasing, or inhibiting the activity of the Ret receptor tyrosine kinase, such as alectinib; h) a compound targeting, decreasing, or inhibiting the activity of the Kit/SCFR receptor tyrosine kinase, such as imatinib; i) a compound targeting, decreasing, or inhibiting the activity of the c-Kit receptor tyrosine kinases, such as imatinib; j) a compound targeting, decreasing, or inhibiting the activity of members of the c-Abl family, their gene-fusion products (e.g. Bcr-Abl kinase) and mutants, such as an N-phenyl-2-pyrimidine-amine derivative, such as imatinib or nilotinib; PD180970; AG957; NSC 680410; PD173955; or dasatinib; k) a compound targeting, decreasing, or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK), such as a staurosporine derivative disclosed in U.S. Pat. No. 5,093,330, such as midostaurin; examples of further compounds include UCN-01, safingol, BAY 43-9006, bryostatin 1, perifosine; ilmofosine; RO 318220 and RO 320432; GO 6976; Isis 3521; LY333531/LY379196; a isochinoline compound; a farnesyl transferase inhibitor; PD184352 or QAN697, or AT7519; abemaciclib; binimetinib; cobimetinib; encorafenib; neratinib; palbociclib; ribociclib; 1) a compound targeting, decreasing or inhibiting the activity of a protein-tyrosine kinase, such as acalabrutinib, imatinib mesylate or a tyrphostin, such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl) methyl]amino}-benzoic acid adamantyl ester; NSC 680410, adaphostin); m) a compound targeting, decreasing, or inhibiting the activity of the epidermal growth factor family of receptor tyrosine kinases (EGFR, ErbB2, ErbB3, ErbB4 as homo- or heterodimers) and their mutants, such as brigatinib, CP 358774, ZD 1839, ZM 105180; trastuzumab, cetuximab, gefitinib, erlotinib, osimertinib, dacomitinib, necitumumab, neratinib, OSI-774, C1-1033, EKB-569, GW-2016, antibodies E1.1, E2.4, E2.5, E6.2, E6.4, E2.11, E6.3 and E7.6.3, and 7H-pyrrolo-[2,3-d]pyrimidine derivatives; n) a compound targeting, decreasing or inhibiting the activity of a phosphatidylinositol 3-kinase (PI3K), such as alpelisib, copanlisib, and duvelisib; and o) a compound targeting, decreasing, or inhibiting the activity of the c-Met receptor.

Nonlimiting exemplary compounds that target, decrease, or inhibit the activity of a protein or lipid phosphatase include inhibitors of phosphatase 1, phosphatase 2A, or CDC25, such as okadaic acid or a derivative thereof.

Further anti-angiogenic compounds include compounds having another mechanism for their activity unrelated to protein or lipid kinase inhibition, e.g., thalidomide and TNP-470.

Additional, nonlimiting, exemplary chemotherapeutic compounds, one or more of which may be used in combination with a Formulation of the Disclosure include: avastin, daunorubicin, adriamycin, Ara-C, VP-16, teniposide, mitoxantrone, idarubicin, carboplatinum, PKC412, 6-mercaptopurine (6-MP), fludarabine phosphate, octreotide, SOM230, FTY720, 6-thioguanine, cladribine, 6-mercaptopurine, pentostatin, hydroxyurea, 2-hydroxy-1H-isoindole-1,3-dione derivatives, 1-(4-chloroanilino)-4-(4-pyridylmethyl)phthalazine or a pharmaceutically acceptable salt thereof, 1-(4-chloroanilino)-4-(4-pyridylmethyl)phthalazine succinate, angiostatin, endostatin, anthranilic acid amides, ZD4190, ZD6474, SU5416, SU6668, bevacizumab, rhuMAb, rhuFab, macugon; FLT-4 inhibitors, FLT-3 inhibitors, VEGFR-2 IgGI antibody, RPI 4610, porfimer sodium, anecortave, triamcinolone, hydrocortisone, 11-a-epihydrocotisol, cortex olone, 17a-hydroxyprogesterone, corticosterone, desoxycorticosterone, testosterone, estrone, dexamethasone, fluocinolone, a plant alkaloid, a hormonal compound and/or antagonist, a biological response modifier, such as a lymphokine or interferon, an antisense oligonucleotide or oligonucleotide derivative, shRNA, and siRNA.

A number of suitable optional therapeutic, e.g., anticancer, agents, are contemplated for use in the therapeutic methods provided herein. Indeed, the methods provided herein can include, but are not limited to, administration of numerous optional therapeutic agents such as: agents that induce apoptosis; polynucleotides (e.g., anti-sense, ribozymes, siRNA); polypeptides (e.g., enzymes and antibodies); biological mimetics (e.g., gossypol or BH3 mimetics); agents that bind (e.g., oligomerize or complex) with a Bcl-2 family protein such as Bax; alkaloids; alkylating agents; antitumor antibiotics; antimetabolites; hormones; platinum compounds; monoclonal or polyclonal antibodies (e.g., antibodies conjugated with anticancer drugs, toxins, defensins), toxins; radionuclides; biological response modifiers (e.g., interferons (e.g., IFN-$\alpha$) and interleukins (e.g., IL-2)); adoptive immunotherapy agents; hematopoietic growth factors; agents that induce tumor cell differentiation (e.g., all-trans-retinoic acid); gene therapy reagents (e.g., antisense therapy reagents and nucleotides); tumor vaccines; angiogenesis inhibitors; proteosome inhibitors: NF-KB modulators; anti-CDK compounds; HDAC inhibitors; and the like. Numerous other examples of optional therapeutic agents such as chemotherapeutic compounds and anticancer therapies suitable for co-administration with the disclosed compounds are known to those skilled in the art.

In certain embodiments, optional therapeutic agents comprise agents that induce or stimulate apoptosis. Agents that induce or stimulate apoptosis include, for example, agents that interact with or modify DNA, such as by intercalating, cross-linking, alkylating, or otherwise damaging or chemically modifying DNA. Agents that induce apoptosis include, but are not limited to, radiation (e.g., X-rays, gamma rays, UV); tumor necrosis factor (TNF)-related factors (e.g., TNF family receptor proteins, TNF family ligands, TRAIL, antibodies to TRAIL-R1 or TRAIL-R2); kinase inhibitors (e.g., epidermal growth factor receptor (EGFR) kinase inhibitor). Additional anticancer agents include: vascular growth factor receptor (VGFR) kinase inhibitor, fibroblast growth factor receptor (FGFR) kinase inhibitor, platelet-derived growth factor receptor (PDGFR) kinase inhibitor, and Bcr-Abl kinase inhibitors (such as GLEEVEC)); antisense molecules; antibodies (e.g., HERCEPTIN, RITUXAN, ZEVALIN, and AVASTIN); anti-estrogens (e.g., raloxifene and tamoxifen); anti-androgens (e.g., flutamide, apalutamide, bicalutamide, finasteride, aminoglutethamide, ketoconazole, and corticosteroids); BCL-2 inhibitors (e.g., venetoclax); cyclooxygenase 2 (COX-2) inhibitors (e.g., celecoxib, meloxicam, NS-398, and non-steroidal anti-inflammatory drugs (NSAIDs)); anti-inflammatory drugs (e.g., butazolidin, DECADRON, DELTASONE, dexamethasone, dexamethasone intensol, DEXONE, HEXADROL, hydroxychloroquine, METICORTEN, ORADEXON, ORASONE, oxyphenbutazone, PEDIAPRED, phenylbutazone, PLAQUENIL, prednisolone, prednisone, PRELONE, and TANDEARIL); and cancer chemotherapeutic drugs (e.g., irinotecan (CAMPTOSAR), CPT-11, fludarabine (FLUDARA), dacarbazine (DTIC), dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; staurosporine, and the like.

In still other embodiments, the therapeutic methods provided herein include administering to a subject having cancer (a cancer patient) therapeutically effective amounts of a Formulation of the Disclosure, an immune checkpoint inhibitor, and at least one additional optional therapeutic agent, e.g., an anti-hyperproliferative or antineoplastic agent selected from alkylating agents, antimetabolites, and natural products (e.g., herbs and other plant and/or animal derived compounds).

Alkylating agents suitable for use in the present methods include, but are not limited to: 1) nitrogen mustards (e.g., mechlorethamine, cyclophosphamide, ifosfamide, melphalan (L-sarcolysin); and chlorambucil); 2) ethylenimines and methylmelamines (e.g., hexamethylmelamine and thiotepa); 3) alkyl sulfonates (e.g., busulfan); 4) nitrosoureas (e.g., carmustine (BCNU); lomustine (CCNU); semustine (methyl-CCNU); and streptozocin (streptozotocin)); and 5) triazenes (e.g., dacarbazine (DTIC; dimethyltriazenoimidazolecarboxamide).

In some embodiments, antimetabolites suitable for use in the present methods include, but are not limited to: 1) folic acid analogs (e.g., methotrexate (amethopterin)); 2) pyrimidine analogs (e.g., fluorouracil (5-fluorouracil; 5-FU), floxuridine (fluorode-oxyuridine; FudR), and cytarabine (cytosine arabinoside)); and 3) purine analogs (e.g., mercaptopurine (6-mercaptopurine; 6-MP), thioguanine (6-thioguanine; TG), and pentostatin (2'-deoxycoformycin)).

In still further embodiments, chemotherapeutic agents suitable for use in the methods of the present disclosure include, but are not limited to: 1) *vinca* alkaloids (e.g., vinblastine (VLB), vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin (cis-DDP) and carboplatin); 7) anthracenediones (e.g., mitoxantrone); 8) substituted ureas (e.g., hydroxyurea); 9) methylhydrazine derivatives (e.g., procarbazine (N-methylhydrazine; MIH)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide).

Any oncolytic agent that is routinely used in a cancer therapy context finds use in the therapeutic methods of the present disclosure. For example, the U.S. Food and Drug Administration (FDA) maintains a formulary of oncolytic agents approved for use in the United States. International counterpart agencies to the FDA maintain similar formularies. Those skilled in the art will appreciate that the "product labels" required on all U.S. approved chemotherapeutics describe approved indications, dosing information, toxicity data, and the like, for the exemplary agents.

Anticancer agents further include compounds which have been identified to have anticancer activity. Examples include, but are not limited to, 3-AP, 12-O-tetradecanoylphorbol-13-acetate, 17AAG, 852A, ABI-007, ABR-217620, ABT-751, ADI-PEG 20, AE-941, AG-013736, AGRO100, alanosine, AMG 706, antibody G250, antineoplastons, AP23573, apaziquone, APC8015, atiprimod, ATN-161, atrasenten, azacitidine, BB-10901, BCX-1777, bevacizumab, BG00001, bicalutamide, BMS 247550, bortezomib, bryostatin-1, buserelin, calaspargase pegol-mknl, calcitriol, CCI-779, CDB-2914, cefixime, cetuximab, CG0070, cilengitide, clofarabine, combretastatin A4 phosphate, CP-675,206, CP-724,714, CpG 7909, curcumin, daratumumab, decitabine, DENSPM, dinutuximab, doxercalciferol, E7070, E7389, ecteinascidin 743, efaproxiral, eflornithine, EKB-569, elotuzumab, enzastaurin, erlotinib, exisulind, fenretinide, flavopiridol, fludarabine, flutamide, fotemustine, FR901228, G17DT, galiximab, gefitinib, genistein, glasdegib, glufosfamide, GTI-2040, histrelin, HKI-272, homoharringtonine, HSPPC-96, hu14.18-interleukin-2 fusion protein, HuMax-CD4, iloprost, imiquimod, infliximab, inotuzumab ozogamicin, interleukin-12, IPI-504, irofulven, ixabepilone, lapatinib, lenalidomide, lestaurtinib, leuprolide, LMB-9 immunotoxin, lonafarnib, luniliximab, lutetium Lu 177 dotatate, mafosfamide, MB07133, MDX-010, MLN2704, mogamulizumab-kpkc, monoclonal antibody 3F8, monoclonal antibody J591, motexafin, moxetumomab pasudotox-tdfk, MS-275, MVA-MUC1-IL2, nilutamide, niraparib, nitrocamptothecin, nolatrexed dihydrochloride, nolvadex, NS-9, O6-benzylguanine, oblimersen sodium, ONYX-015, oregovomab, OSI-774, panitumumab, paraplatin, PD-0325901, pemetrexed, PHY906, pioglitazone, pirfenidone, pixantrone, polatuzumab vedotin-piiq, PS-341, PSC 833, PXD101, pyrazoloacridine, R115777, RAD001, ranpirnase, rebeccamycin analogue, rhuAngiostatin protein, rhuMab 2C4, rosiglitazone, rubitecan, rucaparib, S-1, S-8184, satraplatin, SB-, 15992, SGN-0010, SGN-40, sonidegib, sorafenib, SR31747A, ST1571, SU011248, suberoylanilide hydroxamic acid, suramin, tagraxofusp-erzs, talabostat, talampanel, talazoparib, tariquidar, temsirolimus, TGFa-PE38 immunotoxin, thalidomide, thymalfasin, tipifarnib, tirapazamine, TLK286, trabectedin, trifluridine and tipiracil hydrochloride, trimetrexate glucuronate, TroVax, UCN-1, valproic acid, vinflunine, VNP40101M, volociximab, vorinostat, VX-680, ZD1839, ZD6474, zileuton, and zosuquidar trihydrochloride.

In one embodiment, the optional therapeutic agent comprises one of the anti-cancer drugs or anti-cancer drug combinations listed in Table 3.

TABLE 3

| | | | |
|---|---|---|---|
| Abemaciclib | Abiraterone Acetate | Abraxane (Paclitaxel Albumin-stabilized Nanoparticle Formulation) | ABVD |
| ABVE | ABVE-PC | AC | Acalabrutinib |
| AC-T | Actemra (Tocilizumab) | Adcetris (Brentuximab Vedotin) | ADE |
| Ado-Trastuzumab Emtansine | Adriamycin (Doxorubicin Hydrochloride) | Afatinib Dimaleate | Afinitor (Everolimus) |
| Akynzeo (Netupitant and Palonosetron Hydrochloride) | Aldara (Imiquimod) | Aldesleukin | Alecensa (Alectinib) |
| Alectinib | Alemtuzumab | Alimta (Pemetrexed Disodium) | Aliqopa (Copanlisib Hydrochloride) |
| Alkeran for Injection (Melphalan Hydrochloride) | Alkeran Tablets (Melphalan) | Aloxi (Palonosetron Hydrochloride) | Alunbrig (Brigatinib) |
| Ameluz (Aminolevulinic Acid) | Amifostine | Aminolevulinic Acid | Anastrozole |
| Apalutamide | Aprepitant | Aranesp (Darbepoetin Alfa) | Aredia (Pamidronate Disodium) |
| Arimidex (Anastrozole) | Aromasin (Exemestane) | Arranon (Nelarabine) | Arsenic Trioxide |
| Arzerra (Ofatumumab) | Asparaginase Erwinia chrysanthemi | Atezolizumab | Avastin (Bevacizumab) |
| Avelumab | Axicabtagene Ciloleucel | Axitinib | Azacitidine |
| Azedra (Iobenguane I 131) | Bavencio (Avelumab) | BEACOPP | Beleodaq (Belinostat) |
| Belinostat | Bendamustine Hydrochloride | Bendeka (Bendamustine Hydrochloride) | BEP |
| Besponsa (Inotuzumab Ozogamicin) | Bevacizumab | Bexarotene | Bicalutamide |
| BiCNU (Carmustine) | Binimetinib | Bleomycin | Blinatumomab |
| Blincyto (Blinatumomab) | Bortezomib | Bosulif (Bosutinib) | Bosutinib |
| Brafitovi (Encorafenib) | Brentuximab Vedotin | Brigatinib | BuMel |
| Busulfan | Busulfex (Busulfan) | Cabazitaxel | Cabometyx (Cabozantinib-S-Malate) |
| Cabozantinib-S-Malate | CAF | Calquence (Acalabrutinib) | Campath (Alemtuzumab) |
| Camptosar (Irinotecan Hydrochloride) | Capecitabine | CAPOX | Carac (Fluorouracil--Topical) |
| Carboplatin | CARBOPLATIN-TAXOL | Carfilzomib | Carmustine |
| Carmustine Implant | Casodex (Bicalutamide) | CEM | Cemiplimab-rwlc |
| Ceritinib | Cerubidine (Daunorubicin Hydrochloride) | Cervarix (Recombinant HPV Bivalent Vaccine) | Cetuximab |
| CEV | Chlorambucil | CHLORAMBUCIL-PREDNISONE | CHOP |
| Cisplatin | Cladribine | Clofarabine | Clolar (Clofarabine) |
| CMF | Cobimetinib | Cometriq (Cabozantinib-S-Malate) | Copanlisib Hydrochloride |
| COPDAC | Copiktra (Duvelisib) | COPP | COPP-ABV |
| Cosmegen (Dactinomycin) | Cotellic (Cobimetinib) | Crizotinib | CVP |
| Cyclophosphamide | Cyramza (Ramucirumab) | Cytarabine | Cytarabine Liposome |
| Cytosar-U (Cytarabine) | Dabrafenib | Dacarbazine | Dacogen (Decitabine) |

TABLE 3-continued

| | | | |
|---|---|---|---|
| Dacomitinib | Dactinomycin | Daratumumab | Darbepoetin Alfa |
| Darzalex (Daratumumab) | Dasatinib | Daunorubicin Hydrochloride | Daunorubicin Hydrochloride and Cytarabine Liposome |
| Decitabine | Defibrotide Sodium | Defitelio (Defibrotide Sodium) | Degarelix |
| Denileukin Diftitox | Denosumab | DepoCyt (Cytarabine Liposome) | Dexamethasone |
| Dexrazoxane Hydrochloride | Dinutuximab | Docetaxel | Doxil (Doxorubicin Hydrochloride Liposome) |
| Doxorubicin Hydrochloride | Doxorubicin Hydrochloride Liposome | Dox-SL (Doxorubicin Hydrochloride Liposome) | Durvalumab |
| Duvelisib | Efudex (Fluorouracil—Topical) | Eligard (Leuprolide Acetate) | Elitek (Rasburicase) |
| Ellence (Epirubicin Hydrochloride) | Elotuzumab | Eloxatin (Oxaliplatin) | Eltrombopag Olamine |
| Emend (Aprepitant) | Empliciti (Elotuzumab) | Enasidenib Mesylate | Encorafenib |
| Enzalutamide | Epirubicin Hydrochloride | EPOCH | Epoetin Alfa |
| Epogen (Epoetin Alfa) | Erbitux (Cetuximab) | Eribulin Mesylate | Erivedge (Vismodegib) |
| Erleada (Apalutamide) | Erlotinib Hydrochloride | Erwinaze (Asparaginase Erwinia chrysanthemi) | Ethyol (Amifostine) |
| Etopophos (Etoposide Phosphate) | Etoposide | Etoposide Phosphate | Evacet (Doxorubicin Hydrochloride Liposome) |
| Everolimus | Evista (Raloxifene Hydrochloride) | Evomela (Melphalan Hydrochloride) | Exemestane |
| 5-FU (Fluorouracil Injection) | 5-FU (Fluorouracil--Topical) | Fareston (Toremifene) | Farydak (Panobinostat lactate) |
| Faslodex (Fulvestrant) | FEC | Femara (Letrozole) | Filgrastim |
| Firmagon (Degarelix) | Fludarabine Phosphate | Fluoroplex (Fluorouracil--Topical) | Fluorouracil Injection |
| Fluorouracil--Topical | Flutamide | FOLFIRI | FOLFIRI-BEVACIZUMAB |
| FOLFIRI-CETUXIMAB | FOLFIRINOX | FOLFOX | Folotyn (Pralatrexate) |
| Fostamatinib Disodium | FU-LV | Fulvestrant | Fusilev (Leucovorin Calcium) |
| Gardasil (Recombinant HPV Quadrivalent Vaccine) | Gardasil 9 (Recombinant HPV Nonavalent Vaccine) | Gazyva (Obinutuzumab) | Gefitinib |
| Gemcitabine Hydrochloride | GEMCITABINE-CISPLATIN | GEMCITABINE-OXALIPLATIN | Gemtuzumab Ozogamicin |
| Gemzar (Gemcitabine Hydrochloride) | Gilotrif (Afatinib Dimaleate) | Gleevec (Imatinib Mesylate) | Gliadel Wafer (Carmustine Implant) |
| Glucarpidase | Goserelin Acetate | Granisetron | Granisetron Hydrochloride |
| Granix (Filgrastim) | Halaven (Eribulin Mesylate) | Hemangeol (Propranolol Hydrochloride) | Herceptin (Trastuzumab) |
| HPV Bivalent Vaccine, Recombinant | HPV Nonavalent Vaccine, Recombinant | HPV Quadrivalent Vaccine, Recombinant | Hycamtin (Topotecan Hydrochloride) |
| Hydrea (Hydroxyurea) | Hydroxyurea | Hyper-CVAD | Ibrance (Palbociclib) |
| Ibritumomab Tiuxetan | Ibrutinib | ICE | Iclusig (Ponatinib Hydrochloride) |
| Idarubicin Hydrochloride | Idelalisib | Idhifa (Enasidenib Mesylate) | Ifex (Ifosfamide) |
| Ifosfamide | IL-2 (Aldesleukin) | Imatinib Mesylate | Imbruvica (Ibrutinib) |
| Imfinzi (Durvalumab) | Imiquimod | Imlygic (Talimogene Laherparepvec) | Inlyta (Axitinib) |

TABLE 3-continued

| | | | |
|---|---|---|---|
| Inotuzumab Ozogamicin | Interferon Alfa-2b, Recombinant | Interleukin-2 (Aldesleukin) | Intron A (Recombinant Interferon Alfa-2b) |
| Iobenguane I 131 | Ipilimumab | Iressa (Gefitinib) | Irinotecan Hydrochloride |
| Irinotecan Hydrochloride Liposome | Istodax (Romidepsin) | Ivosidenib | Ixabepilone |
| Ixazomib Citrate | Ixempra (Ixabepilone) | Jakafi (Ruxolitinib Phosphate) | JEB |
| Jevtana (Cabazitaxel) | Kadcyla (Ado-Trastuzumab Emtansine) | Kepivance (Palifermin) | Keytruda (Pembrolizumab) |
| Kisqali (Ribociclib) | Kymriah (Tisagenlecleucel) | Kyprolis (Carfilzomib) | Lanreotide Acetate |
| Lapatinib Ditosylate | Larotrectinib Sulfate | Lartruvo (Olaratumab) | Lenalidomide |
| Lenvatinib Mesylate | Lenvima (Lenvatinib Mesylate) | Letrozole | Leucovorin Calcium |
| Leukeran (Chlorambucil) | Leuprolide Acetate | Levulan Kerastik (Aminolevulinic Acid) | Libtayo (Cemiplimab-rwlc) |
| LipoDox (Doxorubicin Hydrochloride Liposome) | Lomustine | Lonsurf (Trifluridine and Tipiracil Hydrochloride) | Lorbrena (Lorlatinib) |
| Lorlatinib | Lumoxiti (Moxetumomab Pasudotox-tdfk) | Lupron (Leuprolide Acetate) | Lupron Depot (Leuprolide Acetate) |
| Lutathera (Lutetium Lu 177-Dotatate) | Lutetium (Lu 177-Dotatate) | Lynparza (Olaparib) | Marqibo (Vincristine Sulfate Liposome) |
| Matulane (Procarbazine Hydrochloride) | Mechlorethamine Hydrochloride | Megestrol Acetate | Mekinist (Trametinib) |
| Mektovi (Binimetinib) | Melphalan | Melphalan Hydrochloride | Mercaptopurine |
| Mesna | Mesnex (Mesna) | Methotrexate | Methylnaltrexone Bromide |
| Midostaurin | Mitomycin C | Mitoxantrone Hydrochloride | Mogamulizumab-kpkc |
| Moxetumomab Pasudotox-tdfk | Mozobil (Plerixafor) | Mustargen (Mechlorethamine Hydrochloride) | MVAC |
| Myleran (Busulfan) | Mylotarg (Gemtuzumab Ozogamicin) | Nanoparticle Paclitaxel (Paclitaxel Albumin-stabilized Nanoparticle Formulation) | Navelbine (Vinorelbine Tartrate) |
| Necitumumab | Nelarabine | Neratinib Maleate | Nerlynx (Neratinib Maleate) |
| Netupitant and Palonosetron Hydrochloride | Neulasta (Pegfilgrastim) | Neupogen (Filgrastim) | Nexavar (Sorafenib Tosylate) |
| Nilandron (Nilutamide) | Nilotinib | Nilutamide | Ninlaro (Ixazomib Citrate) |
| Niraparib Tosylate Monohydrate | Nivolumab | Nplate (Romiplostim) | Obinutuzumab |
| Odomzo (Sonidegib) | OEPA | Ofatumumab | OFF |
| Olaparib | Olaratumab | Omacetaxine Mepesuccinate | Oncaspar (Pegaspargase) |
| Ondansetron Hydrochloride | Onivyde (Irinotecan Hydrochloride Liposome) | Ontak (Denileukin Diftitox) | Opdivo (Nivolumab) |
| OPPA | Osimertinib | Oxaliplatin | Paclitaxel |
| Paclitaxel Albumin-stabilized Nanoparticle Formulation | PAD | Palbociclib | Palifermin |
| Palonosetron Hydrochloride | Palonosetron Hydrochloride and Netupitant | Pamidronate Disodium | Panitumumab |
| Panobinostat Lactate | Pazopanib Hydrochloride | PCV | PEB |

TABLE 3-continued

| | | | |
|---|---|---|---|
| Pegaspargase | Pegfilgrastim | Peginterferon Alfa-2b | PEG-Intron (Peginterferon Alfa-2b) |
| Pembrolizumab | Pemetrexed Disodium | Perjeta (Pertuzumab) | Pertuzumab |
| Plerixafor | Pomalidomide | Pomalyst (Pomalidomide) | Ponatinib Hydrochloride |
| Portrazza (Necitumumab) | Poteligeo (Mogamulizumab-kpkc) | Pralatrexate | Prednisone |
| Procarbazine Hydrochloride | Procrit (Epoetin Alfa) | Proleukin (Aldesleukin) | Prolia (Denosumab) |
| Promacta (Eltrombopag Olamine) | Propranolol Hydrochloride | Provenge (Sipuleucel-T) | Purinethol (Mercaptopurine) |
| Purixan (Mercaptopurine) | Radium 223 Dichloride | Raloxifene Hydrochloride | Ramucirumab |
| Rasburicase | R-CHOP | R-CVP | Recombinant Human Papillomavirus (HPV) Bivalent Vaccine |
| Recombinant Human Papillomavirus (HPV) Nonavalent Vaccine | Recombinant Human Papillomavirus (HPV) Quadrivalent Vaccine | Recombinant Interferon Alfa-2b | Regorafenib |
| Relistor (Methylnaltrexone Bromide) | R-EPOCH | Retacrit (Epoetin Alfa) | Revlimid (Lenalidomide) |
| Rheumatrex (Methotrexate) | Ribociclib | R-ICE | Rituxan (Rituximab) |
| Rituxan Hycela (Rituximab and Hyaluronidase Human) | Rituximab | Rituximab and Hyaluronidase Human | Rolapitant Hydrochloride |
| Romidepsin | Romiplostim | Rubidomycin (Daunorubicin Hydrochloride) | Rubraca (Rucaparib Camsylate) |
| Rucaparib Camsylate | Ruxolitinib Phosphate | Rydapt (Midostaurin) | Sancuso (Granisetron) |
| Sclerosol Intrapleural Aerosol (Talc) | Siltuximab | Sipuleucel-T | Somatuline Depot (Lanreotide Acetate) |
| Sonidegib | Sorafenib Tosylate | Sprycel (Dasatinib) | STANFORD V |
| Sterile Talc Powder (Talc) | Steritalc (Talc) | Stivarga (Regorafenib) | Sunitinib Malate |
| Sustol (Granisetron) | Sutent (Sunitinib Malate) | Sylatron (Peginterferon Alfa-2b) | Sylvant (Siltuximab) |
| Synribo (Omacetaxine Mepesuccinate) | Tabloid (Thioguanine) | TAC | Tafmlar (Dabrafenib) |
| Tagrisso (Osimertinib) | Talc | Talimogene Laherparepvec | Tamoxifen Citrate |
| Tarabine PFS (Cytarabine) | Tarceva (Erlotinib Hydrochloride) | Targretin (Bexarotene) | Tasigna (Nilotinib) |
| Tavalisse (Fostamatinib Disodium) | Taxol (Paclitaxel) | Taxotere (Docetaxel) | Tecentriq (Atezolizumab) |
| Temodar (Temozolomide) | Temozolomide | Temsirolimus | Thalidomide |
| Thalomid (Thalidomide) | Thioguanine | Thiotepa | Tibsovo (Ivosidenib) |
| Tisagenlecleucel | Tocilizumab | Tolak (Fluorouracil—Topical) | Topotecan Hydrochloride |
| Toremifene | Torisel (Temsirolimus) | Totect (Dexrazoxane Hydrochloride) | TPF |
| Trabectedin | Trametinib | Trastuzumab | Treanda (Bendamustine Hydrochloride) |
| Trexall (Methotrexate) | Trifluridine and Tipiracil Hydrochloride | Trisenox (Arsenic Trioxide) | Tykerb (Lapatinib Ditosylate) |
| Unituxin (Dinutuximab) | Uridine Triacetate | VAC | Valrubicin |

TABLE 3-continued

| | | | |
|---|---|---|---|
| Valstar (Valrubicin) | Vandetanib | VAMP | Varubi (Rolapitant Hydrochloride) |
| Vectibix (Panitumumab) | VeIP | Velcade (Bortezomib) | Vemurafenib |
| Venclexta (Venetoclax) | Venetoclax | Verzenio (Abemaciclib) | Vidaza (Azacitidine) |
| Vinblastine Sulfate | Vincristine Sulfate | Vincristine Sulfate Liposome | Vinorelbine Tartrate |
| VIP | Vismodegib | Vistogard (Uridine Triacetate) | Vitrakvi (Larotrectinib Sulfate) |
| Vizimpro (Dacomitinib) | Voraxaze (Glucarpidase) | Vorinostat | Votrient (Pazopanib Hydrochloride) |
| Vyxeos (Daunorubicin Hydrochloride and Cytarabine Liposome) | Xalkori (Crizotinib) | Xeloda (Capecitabine) | XELIRI |
| XELOX | Xgeva (Denosumab) | Xofigo (Radium 223 Dichloride) | Xtandi (Enzalutamide) |
| Yervoy (Ipilimumab) | Yescarta (Axicabtagene Ciloleucel) | Yondelis (Trabectedin) | Zaltrap (Ziv-Aflibercept) |
| Zarxio (Filgrastim) | Zejula (Niraparib Tosylate Monohydrate) | Zelboraf (Vemurafenib) | Zevalin (Ibritumomab Tiuxetan) |
| Zinecard (Dexrazoxane Hydrochloride) | Ziv-Aflibercept | Zofran (Ondansetron Hydrochloride) | Zoladex (Goserelin Acetate) |
| Zoledronic Acid | Zolinza (Vorinostat) | Zometa (Zoledronic Acid) | Zydelig (Idelalisib) |
| Zykadia (Ceritinib) | Zytiga (Abiraterone Acetate) | | |

For a more detailed description of anticancer agents and other optional therapeutic agents, those skilled in the art are referred to any number of instructive manuals including, but not limited to, the Physician's Desk Reference and to Goodman and Gilman's "Pharmaceutical Basis of Therapeutics" tenth edition, Eds. Hardman et al., 2002.

In another embodiment, the methods of treating cancer provided herein comprise administering a Formulation of the Disclosure to a subject in combination with radiation therapy and, optionally, an immune checkpoint inhibitor. The methods provided herein are not limited by the types, amounts, or delivery and administration systems used to deliver the therapeutic dose of radiation to a patient. For example, the patient may receive photon radiotherapy, particle beam radiation therapy, other types of radiotherapies, and combinations thereof. In some embodiments, the radiation is delivered to the patient using a linear accelerator. In still other embodiments, the radiation is delivered using a gamma knife.

The source of radiation can be external or internal to the patient. External radiation therapy is most common and involves directing a beam of high-energy radiation to a tumor site through the skin using, for instance, a linear accelerator. While the beam of radiation is localized to the tumor site, it is nearly impossible to avoid exposure of normal, healthy tissue. However, external radiation is usually well tolerated by patients. Internal radiation therapy involves implanting a radiation-emitting source, such as beads, wires, pellets, capsules, particles, and the like, inside the body at or near the tumor site including the use of delivery systems that specifically target cancer cells (e.g., using particles attached to cancer cell binding ligands). Such implants can be removed following treatment, or left in the body inactive. Types of internal radiation therapy include, but are not limited to, brachytherapy, interstitial irradiation, intracavity irradiation, radioimmunotherapy, and the like.

The patient may optionally receive radiosensitizers (e.g., metronidazole, misonidazole, intra-arterial Budr, intravenous iododeoxyuridine (IudR), nitroimidazole, 5-substituted-4-nitroimidazoles, 2H-isoindolediones, [[(2-bromoethyl)-amino]methyl]-nitro-1H-imidazole-1-ethanol, nitroaniline derivatives, DNA-affinic hypoxia selective cytotoxins, halogenated DNA ligand, 1,2,4 benzotriazine oxides, 2-nitroimidazole derivatives, fluorine-containing nitroazole derivatives, benzamide, nicotinamide, acridine-intercalator, 5-thiotretrazole derivative, 3-nitro-1,2,4-triazole, 4,5-dinitroimidazole derivative, hydroxylated texaphrins, cisplatin, mitomycin, tiripazamine, nitrosourea, mercaptopurine, methotrexate, fluorouracil, bleomycin, vincristine, carboplatin, epirubicin, doxorubicin, cyclophosphamide, vindesine, etoposide, paclitaxel, heat (hyperthermia), and the like), radioprotectors (e.g., cysteamine, aminoalkyl dihydrogen phosphorothioates, amifostine (WR 2721), IL-1, IL-6, and the like). Radiosensitizers enhance the killing of tumor cells. Radioprotectors protect healthy tissue from the harmful effects of radiation.

Any type of radiation can be administered to a patient, so long as the dose of radiation is tolerated by the patient without unacceptable negative side-effects. Suitable types of radiotherapy include, for example, ionizing (electromagnetic) radiotherapy (e.g., X-rays or gamma rays) or particle beam radiation therapy (e.g., high linear energy radiation). Ionizing radiation is defined as radiation comprising particles or photons that have sufficient energy to produce ionization, i.e., gain or loss of electrons (as described in, for example, U.S. Pat. No. 5,770,581 incorporated herein by reference in its entirety). The effects of radiation can be at least partially controlled by the clinician. In one embodiment, the dose of radiation is fractionated for maximal target cell exposure and reduced toxicity.

In one embodiment, the total dose of radiation administered to a patient is about 0.01 Gray (Gy) to about 100 Gy. In another embodiment, about 10 Gy to about 65 Gy (e.g., about 15 Gy, 20 Gy, 25 Gy, 30 Gy, 35 Gy, 40 Gy, 45 Gy, 50 Gy, 55 Gy, or 60 Gy) are administered over the course of treatment. While in some embodiments a complete dose of radiation can be administered over the course of one day, the total dose is ideally fractionated and administered over several days. Desirably, radiotherapy is administered over the course of at least about 3 days, e.g., at least 5, 7, 10, 14, 17, 21, 25, 28, 32, 35, 38, 42, 46, 52, or 56 days (about 1-8 weeks). Accordingly, a daily dose of radiation will comprise approximately 1-5 Gy (e.g., about 1 Gy, 1.5 Gy, 1.8 Gy, 2 Gy, 2.5 Gy, 2.8 Gy, 3 Gy, 3.2 Gy, 3.5 Gy, 3.8 Gy, 4 Gy, 4.2 Gy, or 4.5 Gy), or 1-2 Gy (e.g., 1.5-2 Gy). The daily dose of radiation should be sufficient to induce destruction of the targeted cells. If stretched over a period, in one embodiment, radiation is not administered every day, thereby allowing the animal to rest and the effects of the therapy to be realized. For example, radiation desirably is administered on 5 consecutive days, and not administered on 2 days, for each week of treatment, thereby allowing 2 days of rest per week. However, radiation can be administered 1 day/week, 2 days/week, 3 days/week, 4 days/week, 5 days/week, 6 days/week, or all 7 days/week, depending on the animal's responsiveness and any potential side effects. Radiation therapy can be initiated at any time in the therapeutic period. In one embodiment, radiation is initiated in week 1 or week 2, and is administered for the remaining duration of the therapeutic period. For example, radiation is administered in weeks 1-6 or in weeks 2-6 of a therapeutic period comprising 6 weeks for treating, for instance, a solid tumor. Alternatively, radiation is administered in weeks 1-5 or weeks 2-5 of a therapeutic period comprising 5 weeks. These exemplary radiotherapy administration schedules are not intended, however, to limit the methods provided herein.

VI. Methods of Making Lyophilates of the Disclosure

In another embodiment, the disclosure provides a method of making a Lyophilate of the Disclosure, the method comprising:

(i) preparing a pre-lyophilization solution comprising Compound 1 and water;
(ii) cooling the pre-lyophilization solution until it is frozen or partially frozen; and
(iii) applying a vacuum to the frozen or partially frozen pre-lyophilization solution to give the lyophilate.

In another embodiment, the pre-lyophilization solution further comprises ethanol.

In another embodiment, the pre-lyophilization solution further comprises t-butanol (TBA).

In another embodiment, the disclosure provides a method of making a Lyophilate of the Disclosure, the method comprising:

(i) dissolving Compound 1 in a mixture of t-butanol, ethanol, and water at a temperature of about 20° C. to about 50° C. to give a pre-lyophilization solution;
(ii) cooling the pre-lyophilization solution until it is frozen or partially frozen; and
(iii) applying a vacuum to the frozen or partially frozen pre-lyophilization solution to give the lyophilate.

In another embodiment, Compound 1 is dissolved in a mixture of t-butanol, ethanol, and water at a temperature of about 25° C. to about 35° C. In another embodiment, the temperature is about 25° C. to about 30° C. In another embodiment, the temperature is about 25° C. In another embodiment, the temperature is about 30° C.

In another embodiment, the pre-lyophilization solution further comprises polyvinylpyrrolidone. In another embodiment, the pre-lyophilization solution further comprises L-histidine. In another embodiment, the pre-lyophilization solution further comprises ethanol, t-butanol, polyvinylpyrrolidone, and L-histidine.

In another embodiment, the concentration of Compound 1 in the pre-lyophilization solution is about 1 mg/mL to about 15 mg/mL. In another embodiment, the concentration of Compound 1 in the pre-lyophilization solution is about 10 mg/mL.

VII. Methods of Making Pharmaceutical Compositions

In another embodiment, the disclosure provides a method of making a Pharmaceutical Composition of the Disclosure, the method comprising dissolving, i.e., reconstituting, a Lyophilate of the Disclosure in a solvent.

In another embodiment, the solvent comprises water e.g., WFI.

In another embodiment, the solvent comprises water and ethanol.

In another embodiment, the solvent comprises about 40% to about 60% ethanol and about 40% to about 60% water.

In another embodiment, the solvent comprises about 70% to about 90% ethanol and about 10% to about 30% water.

In another embodiment, the solvent comprises about 75% to about 85% ethanol and about 15% to about 25% water.

In another embodiment, the solvent comprises about 40% ethanol and about 60% water. In another embodiment, the solvent comprises about 45% ethanol and about 55% water. In another embodiment, the solvent comprises about 50% ethanol and about 50% water. In another embodiment, the solvent comprises about 55% ethanol and about 45% water. In another embodiment, the solvent comprises about 60% ethanol and about 40% water. In another embodiment, the solvent comprises about 65% ethanol and about 35% water. In another embodiment, the solvent comprises about 70% ethanol and about 30% water. In another embodiment, the solvent comprises about 75% ethanol and about 25% water. In another embodiment, the solvent consists of about 80% ethanol and about 20% water. In another embodiment, the solvent comprises about 85% ethanol and about 15% water. In another embodiment, the solvent comprises about 90% ethanol and about 10% water.

VIII. Methods of Making Pharmaceutical Formulations

In another embodiment, the disclosure provides a method of making a Pharmaceutical Formulation of the Disclosure, the method comprising admixing a Pharmaceutical Composition of the Disclosure with a diluent. In another embodiment, the diluent is normal saline.

IX. Kits

In another embodiment, the disclosure provides a kit comprising a Lyophilate of the Disclosure packaged as single unit dose in a vial. In another embodiment, the vial has a stopper and a cap. In another embodiment, the vial is glass.

In another embodiment, the disclosure provides a kit comprising a Lyophilate of the Disclosure packaged as single unit dose in a vial for the treatment of cancer in a subject.

In another embodiment, the kit further comprises instructions for reconstituting the lyophilate in a solvent to give a Pharmaceutical composition of the Disclosure.

In another embodiment, the kit further comprises instructions for admixing the Pharmaceutical Composition of the Disclosure with a diluent to give a Pharmaceutical Formulation of the Disclosure.

In another embodiment, the kit further comprises instructions for administering the Pharmaceutical Formulation of the Disclosure to a subject.

In another embodiment, the kit further comprises an optional therapeutic agent.

In another embodiment, the kit further comprises a device suitable for administering the Pharmaceutical Formulation of the Disclosure to a subject according to the intended route of administration, e.g., intravenously.

The present disclosure is also drawn to the following particular embodiments:

Embodiment 1. A lyophilate comprising (S)-isopropyl 2-((S)-2-acetamido-3-(1H-indol-3-yl)propanamido)-6-diazo-5-oxohexanoate.

Embodiment 2. The lyophilate of Embodiment 1 further comprising a stabilizing agent.

Embodiment 3. The lyophilate of Embodiment 2, wherein the (S)-isopropyl 2-((S)-2-acetamido-3-(1H-indol-3-yl) propanamido)-6-diazo-5-oxohexanoate/stabilizing agent weight ratio is about 10 to about 0.1.

Embodiment 4. The lyophilate of Embodiment 3, wherein the (S)-isopropyl 2-((S)-2-acetamido-3-(1H-indol-3-yl) propanamido)-6-diazo-5-oxohexanoate/stabilizing agent weight ratio is about 5 to about 0.5.

Embodiment 5. The lyophilate of Embodiment 4, wherein the (S)-isopropyl 2-((S)-2-acetamido-3-(1H-indol-3-yl) propanamido)-6-diazo-5-oxohexanoate/stabilizing agent weight ratio is about 1.

Embodiment 6. The lyophilate of any one of Embodiments 2-5, wherein the stabilizing agent is polyvinylpyrrolidone.

Embodiment 7. The lyophilate of any one of Embodiments 1-6 further comprising a buffering agent.

Embodiment 8. The lyophilate of Embodiment 7, wherein the (S)-isopropyl 2-((S)-2-acetamido-3-(1H-indol-3-yl) propanamido)-6-diazo-5-oxohexanoate/buffering agent weight ratio is about 20 to about 1.

Embodiment 9. The lyophilate of Embodiment 8, wherein the (S)-isopropyl 2-((S)-2-acetamido-3-(1H-indol-3-yl) propanamido)-6-diazo-5-oxohexanoate/buffering agent weight ratio is about 15 to about 5.

Embodiment 10. The lyophilate of Embodiment 9, wherein the (S)-isopropyl 2-((S)-2-acetamido-3-(1H-indol-3-yl)propanamido)-6-diazo-5-oxohexanoate/buffering agent weight ratio is about 10.

Embodiment 11. The lyophilate of any one of Embodiments 7-10, wherein buffering agent is L-histidine.

Embodiment 12. The lyophilate of Embodiment 1 comprising about 63 mg of (S)-isopropyl 2-((S)-2-acetamido-3-(1H-indol-3-yl)propanamido)-6-diazo-5-oxohexanoate.

Embodiment 13. The lyophilate of Embodiment 12 further comprising about 63 mg of polyvinylpyrrolidone.

Embodiment 14. The lyophilate of Embodiments 12 or 13 further comprising about 6.5 mg of L-histidine.

Embodiment 15. A pharmaceutical composition comprising the lyophilate of any one of Embodiments 1-14, wherein the lyophilate is reconstituted in a solvent.

Embodiment 16. The pharmaceutical composition of Embodiment 15, wherein the solvent comprises ethanol and water.

Embodiment 17. The pharmaceutical composition of Embodiment 16, wherein the solvent comprises about 70% to about 90% ethanol and about 10% to about 30% water.

Embodiment 18. The pharmaceutical composition of Embodiment 17, wherein the solvent comprises about 75% to about 85% ethanol and about 15% to about 25% water.

Embodiment 19. The pharmaceutical composition of Embodiment 18, wherein the solvent consists of about 80% ethanol and about 20% water.

Embodiment 20. The pharmaceutical composition of any one of Embodiments 15-19, wherein the (S)-isopropyl 2-((S)-2-acetamido-3-(1H-indol-3-yl)propanamido)-6-diazo-5-oxohexanoate concentration is about 15 mg/mL.

Embodiment 21. A pharmaceutical formulation comprising the pharmaceutical composition of any one of Embodiments 15-20 and a diluent.

Embodiment 22. The pharmaceutical formulation of Embodiment 20, wherein the diluent is normal saline.

Embodiment 23. The pharmaceutical formulation of Embodiment 22, wherein the (S)-isopropyl 2-((S)-2-acetamido-3-(1H-indol-3-yl)propanamido)-6-diazo-5-oxohexanoate concentration is about 0.3 mg/mL.

Embodiment 24. A method for treating cancer in a subject in need thereof, the method comprising administering a therapeutically effective amount of the pharmaceutical formulation of any one of Embodiments 20-23 to the subject.

Embodiment 25. The method of Embodiment 24, wherein the pharmaceutical formulation is administered intravenously to the subject.

Embodiment 26. The method of Embodiments 24 or 25 further comprising administering an optional therapeutic agent to the subject.

Embodiment 27. A method of making the lyophilate of Embodiment 1, the method comprising:

(i) preparing a pre-lyophilization solution comprising (S)-isopropyl 2-((S)-2-acetamido-3-(1H-indol-3-yl) propanamido)-6-diazo-5-oxohexanoate and water;

(ii) cooling the pre-lyophilization solution until it is frozen; and (iii) applying a vacuum to the frozen pre-lyophilization solution to give the lyophilate.

Embodiment 28. The method of Embodiment 27, wherein the pre-lyophilization solution further comprises ethanol.

Embodiment 29. The method of Embodiments 27 or 28, wherein the pre-lyophilization solution further comprises t-butanol.

Embodiment 30. The method of any one of Embodiments 27-29, wherein the pre-lyophilization solution further comprises polyvinylpyrrolidone.

Embodiment 31. The method of any one of Embodiments 27-30, wherein the pre-lyophilization solution further comprises L-histidine.

Embodiment 32. A method of making the pharmaceutical composition of Embodiment 15, the method comprising dissolving the lyophilate in a solvent.

Embodiment 33. The method of Embodiment 32, wherein the solvent comprises water and ethanol.

Embodiment 34. A method of making the pharmaceutical formulation of Embodiment 21, the method comprising admixing the pharmaceutical composition with a diluent.

Embodiment 35. The method of Embodiment 34, wherein the diluent is normal saline.

Embodiment 36. A kit comprising the lyophilate of any one of Embodiments 1-13 packaged as single unit dose in a vial.

Embodiment 37. The kit of Embodiment 36 for the treatment of cancer in a subject in need thereof.

Embodiment 38. The kit of Embodiment 37 further comprising instructions for reconstituting the lyophilate in a solvent to give a pharmaceutical composition.

Embodiment 39. The kit of Embodiment 38 further comprising instructions for admixing the pharmaceutical composition with a diluent to give a pharmaceutical formulation.

Embodiment 40. The kit of Embodiment 38 further comprising instructions for administering the pharmaceutical formulation to the subject.

X. Definitions

The terms "(S)-isopropyl 2-((S)-2-acetamido-3-(1H-indol-3-yl)propanamido)-6-diazo-5-oxohexanoate" and "Compound 1" refer to a prodrug of 6-diazo-5-oxo-L-norleucine (DON) having the following structure:

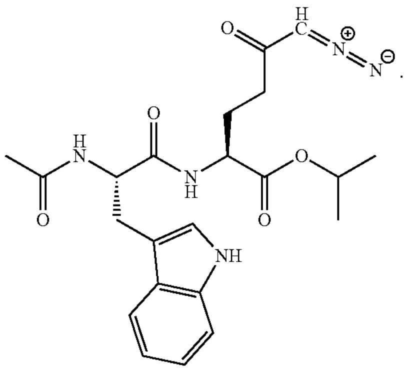 [SMILES: CC(=O)N[C@@H](Cc1c[nH]c2ccccc12)C(=O)N[C@@H](CCC(=O)C=[N+]=[N-])C(=O)OC(C)C]

Compound 1 is described in U.S. Pat. No. 10,336,778 B2.

The term "lyophilate" as used herein refers to a powder obtained by lyophilization.

The terms "lyophilization," "lyophilizing," and "lyophilized" as used herein refer to a freeze-drying process by which Compound 1 is frozen and, while still in the frozen state, water and other solvents, if present, are removed by sublimation under vacuum. Compound 1 may be lyophilized in the presence of other agents, e.g., stabilizing agents, buffering agents, in order to enhance the properties of the lyophilate thus obtained.

The terms "reconstitute," "reconstituted," or "reconstitution" as used herein refer to dissolving a lyophilate in a pharmaceutically acceptable solvent to give a solution. In one embodiment, this solution is diluted before intravenous administration to a subject.

The term "solvent" as used herein refers to a liquid e.g., water, or mixture of liquids, e.g., water and ethanol, that is suitable for administration to a subject as part of a pharmaceutical composition or formulation. In one embodiment, the solvent comprises a combination of water and one, two, three, or four additional pharmaceutically acceptable water miscible solvents, e.g., dioxolanes, dimethylacetamide, butylene glycol, polyethylene glycol, glycerin, ethanol, and the like, or a combination thereof. In another embodiment, the solvent is a combination of water and one additional pharmaceutically acceptable water miscible solvent. In another embodiment, the solvent is a combination of water and ethanol. In another embodiment, the solvent comprises a combination of water and one, two, three, or four additional pharmaceutically acceptable water immiscible solvents, e.g., peanut oil, ethyl oleate, and the like. In another embodiment, the solvent comprises about 40% to about 60% of water and about 40% to about 60% of a water miscible solvent, e.g., ethanol. In another embodiment, the solvent comprises about 10% to about 30% of water and about 70% to about 90% of a water miscible solvent, e.g., ethanol. In another embodiment, the solvent comprises about 15% to about 25% of water and about 75% to about 85% of a water miscible solvent. In another embodiment, the solvent consists essentially of about 20% of water and about 80% of a water miscible solvent. In another embodiment, the solvent consists essentially of about 50% of water and about 50% of a water miscible solvent. In another embodiment, the solvent consists of about 50% of water and about 50% of a water miscible solvent.

The term "stabilizing agent" refers to a pharmaceutically acceptable excipient that protects Compound 1 from degradation before, during, or after lyophilization, e.g., during storage of the lyophilate prior to administration to a subject. Stabilizing agents may simultaneously act as bulking agents. Exemplary non-limiting stabilizing agents include sucrose, trehalose, mannitol, polyvinylpyrrolidone (PVP), polyvinylpyrrolidone-vinylacetate copolymer (PVP-VA), hydroxypropylmethylcellulose (HPMC), pyromellose-acetate-succinate (HPMCAS), dextrose, and glycine, and mixtures thereof.

The term "buffering agent" refers to a pharmaceutically acceptable excipient that helps maintain the pH during lyophilization and after reconstitution of the resulting lyophilate. Exemplary non-limiting buffering agents include glycine, L-histine, phosphate, acetic acid, lactic acid, citric acid, and Tris.

The term "diluent" as used herein refers to a liquid used to dilute a pharmaceutical composition before intravenous administration to a subject. In one embodiment, the diluent is normal saline, 5% dextrose, lactated Ringer's solution, or any other sterile fluid designed to be compatible with administration by intravenous infusion, to humans. In another embodiment, the diluent is normal saline, e.g., 0.9% Sodium Chloride Injection, USP.

The term "weight ratio" as used herein refers to mass of Compound 1 divided by the mass of another agent, e.g., a stabilizing agent or a buffering agent, in the lyophilate. For example, the Compound 1/stabilizing agent weight ratio in a lyophilate comprising 63 mg of Compound 1 and 63 mg of polyvinylpyrrolidone (PVP) is 1. The Compound 1/buffering agent weight ratio in a lyophilate comprising 63 mg of Compound 1, 63 mg of polyvinylpyrrolidone (PVP), and 6.5 mg of L-histidine is 9.7.

The terms "intermittent dose administration," "intermittent dosing schedule," and similar terms as used herein refer to non-continuous administration of a Pharmaceutical Formulation of the Disclosure to a subject. Intermittent dose administration regimens useful in the present disclosure encompass any discontinuous administration regimen that provides a therapeutically effective amount of a Pharmaceutical Formulation of the Disclosure to a subject in need thereof. Intermittent dosing regimens can use equivalent, lower, or higher doses of a Pharmaceutical Formulation of the Disclosure than would be used in continuous dosing regimens. Advantages of intermittent dose administration include, but are not limited to, improved safety, decreased toxicity, e.g., decreased weight loss, increased exposure, increased efficacy, and/or increased subject compliance. These advantages may be realized when a Pharmaceutical Formulation of the Disclosure is administered as a single agent or when administered in combination with one or more additional therapeutic agents, e.g., an immune checkpoint inhibitor.

In one embodiment, a Pharmaceutical Formulation of the Disclosure is administered to the subject according to an intermittent dosing schedule to treat cancer. In another embodiment, the intermittent dosing schedule increases the therapeutic index of the Pharmaceutical Formulation of the Disclosure. The therapeutic index is a comparison of the amount of the Pharmaceutical Formulation of the Disclosure that causes the therapeutic effect, e.g., decrease in tumor mass, increase in time to tumor progression, and/or increase in subject survival time, to the amount that causes toxicity, e.g. body weight loss.

In one embodiment, the Pharmaceutical Formulation of the Disclosure is administered to the subject every other day.

In another embodiment, the Pharmaceutical Formulation of the Disclosure is administered to the subject once a week.

In another embodiment, the Pharmaceutical Formulation of the Disclosure is administered to the subject twice a week on consecutive days, e.g., on Monday and Tuesday.

In another embodiment, the Pharmaceutical Formulation of the Disclosure is administered to the subject twice a week on non-consecutive days, e.g., on Monday and Wednesday.

In another embodiment, the Pharmaceutical Formulation of the Disclosure is administered to the subject three times a week on consecutive days, e.g., on Monday, Tuesday, and Wednesday.

In another embodiment, the Pharmaceutical Formulation of the Disclosure is administered to the subject three times a week on non-consecutive days, e.g., on Monday, Wednesday, and Friday.

"Concurrent administration," "administered in combination," "simultaneous administration," and similar phrases mean that two or more agents are administered concurrently to the subject being treated. By "concurrently," it is meant that each agent is administered either simultaneously or sequentially in any order at different points in time. However, if not administered simultaneously, it is meant that they are administered to an individual in a sequence and sufficiently close in time so as to provide the desired therapeutic effect and can act in concert. For example, a Pharmaceutical Formulation of the Disclosure can be administered to a subject at the same time or sequentially in any order at different points in time as the optional therapeutic agent. A Pharmaceutical Formulation of the Disclosure and an optional therapeutic agent can be administered separately, in any appropriate form and by any suitable route, e.g., by IV injection, respectively. When a Pharmaceutical Formulation of the Disclosure and an optional therapeutic agent are not administered concurrently, it is understood that they can be administered in any order to a subject in need thereof. For example, a Pharmaceutical Formulation of the Disclosure can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, or more before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, or more after) an optional therapeutic agent.

The terms "a" and "an" refer to one or more than one.

The term "about," as used herein, includes the recited number ±10%. Thus, "about 10" means 9 to 11.

EXAMPLE 1

Preparation of Lyophilate Comprising Compound 1 in Unit Dosage Form

1. Dissolution to Give a Pre-Lyophilization Solution

Pre-lyophilization solution #1: First, 189 g of Compound 1 (purity≥97%) is weighed out. Second, 189 g of polyvinylpyrrolidone (PVP) (BASF Kollidon 12PF) and 19.5 g of L-histidine are dissolved in water, and the solution is titrated to pH 6.7 with 20.9 mL of 1 N HCl. Third, the aqueous solution of PVP and L-histidine is mixed with 3444 g of t-butanol and 994.1 g ethanol. Fourth, the pre-weighed Compound 1 is dissolved to give a pre-lyophilization solution. The dissolution of Compound 1 takes place at room temperature and may take several hours.

Pre-lyophilization solution #2: First, 126 g of Compound 1 (purity≥97%) is weighed out. Second, 189 g of polyvinylpyrrolidone (PVP) (BASF Kollidon 12PF) and 19.5 g of L-histidine are dissolved in water, and the solution is titrated to pH 6.7 with 20.9 mL of 1 N HCl. Third, the aqueous solution of PVP and L-histidine is mixed with 3440 g of t-butanol and 994 g ethanol. Fourth, the pre-weighed Compound 1 is dissolved to give a pre-lyophilization solution and the solution is brought to a volume of 12.6 L. The dissolution of Compound 1 takes place at 30° C. and may take several hours.

2. Sterile Filtration: The pre-lyophilization solution is sterile filtered, e.g., using a Millipore Durapore 0.22 micron capsule filter.
3. Filling: The sterile solution is transferred into the isolator glove box for vial filling and partial insertion of the stoppers.
4. Transfer: The filled vials are transferred into a lyophilizer while maintaining the aseptic environment of the partially stoppered vial. The vial stoppers are seated automatically, and the stoppered vials are transferred to an isolator for capping.
5. Freezing/drying:

Program #1: The Initial shelf temperature is room temperature. The shelf temperature is decreased to −40° C. at a rate of 2.5° C./min (about 25 min). When the shelf temperature reaches −40° C., the temperature is held for 100 min. When the product temperature reaches −35° C., the temperature is held for 30 min. The freezing process takes approximately 4.5 h. The frozen pre-lyophilization solution is dried under vacuum. The freezing/drying is accomplished according to the following program.

| Step | Program Time (h) | Shelf Temperature (° C.) | Vacuum (mTorr) |
|---|---|---|---|
| Freezing | 0 to 4.5 h | RT → −40° C. | Ambient Pressure |
| −40° C. Hold | 4.5 to 49 h | −40° C. | 45 |
| Ramp to 0° C. | 49 to 54 h | Ramp to 0° C. | 45 |
| 0° C. Hold | 54 to 66 h | 0° C. | 45 |

-continued

| Step | Program Time (h) | Shelf Temperature (° C.) | Vacuum (mTorr) |
|---|---|---|---|
| Ramp to 25° C. | 66 to 67 h | Ramp to 25° C. | 45 |
| 25° C. Hold | 67 to 95 h | 25° C. | 45 |

Program #2: The initial shelf temperature is room temperature. The shelf temperature is decreased to −40° C., and the pressure is dropped to 45 mTorr. This condition is held for 44.5 h. Then, the shelf temperature is ramped up to 0° C. over 5 hours and held at that temperature for 12 hours. Then, the shelf temperature is ramped up to 35° C. over 1 h and held at that temperature for 28 h. The shelf temperature is ramped back to room temperature over 1 h prior to nitrogen equilibration and then insertion of stoppers. The freezing/drying is accomplished according to the following program.

| Step | Program Time (h) | Step Time (h) | Shelf Temperature (° C.) | Vacuum (mTorr) |
|---|---|---|---|---|
| Freezing | 0 to 6.5 | 6.5 | −40° C. | Ambient Pressure |

-continued

| Step | Program Time (h) | Step Time (h) | Shelf Temperature (° C.) | Vacuum (mTorr) |
|---|---|---|---|---|
| −40° C. Hold | 6.5 to 51 h | 44.5 | −40° C. | 45 |
| Ramp to 0° C. | 51 to 56 h | 5 | Ramp to 0° C. | 45 |
| 0° C. Hold | 56 to 68 h | 12 | 0° C. | 45 |
| Ramp to 35° C. | 68 to 69 h | 1 | Ramp to 35° C. | 45 |
| 35° C. Hold | 69 to 97 h | 28 | 35° C. | 45 |
| Ramp to RT and Nitrogen Fill | 97 to 98 h | 1 | Ramp to RT and Nitrogen Fill | Ambient Pressure Following Nitrogen Fill |

The chemical purity of Compound 1 in the lyophilate thus obtained is greater than or equal to 97%.

EXAMPLE 2

Reconstitution Trials

The reconstitution of lyophilates comprising 15 mg/mL of Compound 1 and various excipients (L1-L9) with various solvents are summarized in Tables 4 and 5.

TABLE 4

| Solvent | L1 15 mg/mL PVP | L2 15 mg/mL PVP; 15 mg/mL sucrose | L3 15 mg/mL PVP; 5 mg/mL sucrose | L4 15 mg/mL of sucrose | L5 30 mg/mL of sucrose | L6 No excipient(s) |
|---|---|---|---|---|---|---|
| Ethanol | Instant clear in 2 mL | | | | | More than 1 min in 2 mL |
| 50% Ethanol/50% PEG 400 | 30 inversions to be clear in 2 mL | | 30 inversions to be clear in 4 mL | | | More than 1 min in 4 mL |
| 45% Ethanol/45% PEG 400/10% WFI | 30 inversions to be clear in 2 mL | 30 inversions to be clear in 2 mL | 30 inversions to be clear in 2 mL | 60 inversions to be clear in 2 mL | More than 1 min in 4 mL | More than 1 min in 4 mL |
| 50% Ethanol/50% Propylene Glycol | 30 inversions to be clear in 2 mL | | 30 inversions to be clear in 2 mL | | | More than 1 min in 4 mL |
| 45% Ethanol/45% Propylene Glycol/10% WFI | More than 1 min in 4 mL | More than 1 min in 4 mL | More than 1 min in 4 mL | 60 inversions not clear in 2 mL, clear in 4 mL | More than 1 min in 4 mL | More than 1 min in 4 mL |
| 10% Ethanol/ 67.5% Propylene Glycol/ 22.5% WFI | More than 1 min in 4 mL | More than 1 min in 4 mL | More than 1 min in 4 mL | More than 1 min in 4 mL | | More than 1 min in 4 mL |
| 90% Ethanol/10% WFI | | | | Clear with 4 mL, but not with 2 mL | Not clear with 4 mL | |

TABLE 4-continued

| Solvent | L1 15 mg/mL PVP | L2 15 mg/mL PVP; 15 mg/mL sucrose | L3 15 mg/mL PVP; 5 mg/mL sucrose | L4 15 mg/mL of sucrose | L5 30 mg/mL of sucrose | L6 No excipient(s) |
|---|---|---|---|---|---|---|
| 80% Ethanol/20% WFI | | | | 60 inversions to be clear in 2 mL | 30 inversions to be clear in 2 mL | |
| 95% Ethanol/5% WFI | | | | Clear with 4 mL 60 invert, but not with 2 mL | Not clear with 4 mL | |

TABLE 5

| Solvent | L1 15 mg/mL PVP | L7 7.5 mg/mL PVP | L5 30 mg/mL sucrose | L4 15 mg/mL sucrose | L8 7.5 mg/mL PVP; 5 mg/mL sucrose | L9 7.5 mg/mL PVP; 5 mg/mL mannitol |
|---|---|---|---|---|---|---|
| 10% ethanol/67.5% Propylene Glycol | 60 inversions clear in 2 mL | 120 inversions not clear in 4 mL (large amount debris) | 90 inversions clear in 2 mL | 120 inversions clear in 2 mL | 120 inversions not clear in 2 mL (debris observed) | 120 inversions not clear in 4 mL (big chunks) |
| 15% ethanol/67.5% Propylene Glycol with WFI as remainder | 120 inversions clear in 2 mL | 120 inversions not clear in 4 mL (debris) | 60 inversions clear in 2 mL | 90 inversions clear in 2 mL | 120 inversions not clear in 2 mL (debris) | 120 inversions not clear in 4 mL (big chunks) |
| 10% ethanol/37.5% Propylene Glycol/30% PEG 400 with WFI as remainder | 120 inversions not clear in 2 mL | 120 inversions not clear in 4 mL (chunks) | 120 inversions almost clear in 2 mL (very few debris) | 120 inversions clear in 2 mL | N/A | 120 inversions not clear in 4 mL (big chunks) |
| 15% ethanol/37.5% Propylene Glycol/30% PEG 400 with WFI as remainder | 90 inversions clear in 2 mL | 120 inversions not clear in 2 mL (debris) | 120 inversions clear in 2 mL (very few debris) | 120 inversions not clear in 2 mL (debris) | 90 inversions almost clear in 2 mL (very few debris) | 120 inversions not clear in 4 mL (big chunks) |
| 50% Ethanol/50% PEG 400 | 20 inversions clear in 2 mL | 30 inversions clear in 2 mL | 90 inversions clear in 2 mL (turn hazy after 1 hour) | 90 inversions clear in 2 mL (precipitation observed overnight) | 30 inversions clear in 2 mL | 120 inversions not clear in 4 mL (hazy and debris) |
| 80% Ethanol/20% WFI | 20 inversions clear in 2 mL | 20 inversions clear in 2 mL | 30 inversions clear in 2 mL | 60 inversions clear in 2 mL | 20 inversions clear in 2 mL | 120 inversions clear in 2 mL |
| 50% Ethanol/50% Propylene Glycol | 20 inversions clear in 2 mL | 60 inversions clear in 2 mL | 30 inversions clear in 4 mL | 120 inversions clear in 2 mL | 60 inversions clear in 2 mL | 120 inversions not clear in 4 mL (hazy and debris) |

EXAMPLE 3

Compounding, Lyophilization, Reconstitution, and Dilution

The amounts of Compound 1, PVP, histidine, ethanol, t-butanol, and other ingredients for preparing a lyophilate of Compound 1 are provided in Table 6.

TABLE 6

| Ingredient | Concentration (g/L) | Amount |
|---|---|---|
| Compound 1 (g) | 10.0 | 0.0420 |
| PVP (g) | 15.0 | 0.0630 |
| Histidine (g) | 1.55 | 0.0065 |
| Ethanol (g) | 78.9 | 0.331 |
| Ethanol (L) (d = 0.789) | | 0.000420 |
| t-Butanol (g) | 273.0 | 1.147 |
| t-Butanol (L) (d = 0.780) | | 0.00147 |
| QS to (with WFI) (g) | | 3.95 |
| QS to (with WFI) (L) | | 0.0042 |
| 1M HCl (titrate to pH 6.6-6.8) (mL) | | 0.0070 |

The procedure to prepare a Pharmaceutical Formulation of the Disclosure for administration to a subject was as follows:

1. Dissolution of Drug Product Components to Give a Pre-Lyophilization Solution:

First, PVP and histidine were dissolved in 90% of the required water for injection (WFI) at room temperature, and this solution was titrated to the target pH of 6.6 to 6.8 with a 1 M HCl solution.

Second, the aqueous solution comprising PVP and histidine was mixed with warm t-butanol and ethanol.

Third, Compound 1 was dissolved in the solution at 30° C. After dissolution, the solution was cooled to room temperature (20-22° C.).

Fourth, the solution was QSed to the target weight with room temperature WFI to give a "Compound 1 solution" having a Compound 1 concentration of about 10 mg/mL.

2. Sterile Filtration:

The Compound 1 solution was sterile filtered using redundant Millipore Durapore 0.22 micron capsule filters for filing into a vial. The filter areas are:

| Filter | Millipak 20 | Millipak 100 | Millipak 200 |
|---|---|---|---|
| Filter Area ($cm^2$) | 100 | 500 | 1000 |
| Volume (L) | 2.5 | 12.5 | 25 |
| Volume/Area ($L/cm^2$) | 0.0250 | 0.0250 | 0.0250 |

3. Lyophilization:

The lyophilization cycle proceeded in 4 steps: ethanol removal at −40° C., primary drying at 0° C., secondary drying at 35° C., and return of vials to room temperature as described in EXAMPLE 1, program 2. The lyocycle was approximately 98 h in total.

Upon completion of drying the vacuum was neutralized with sterile filtered nitrogen to give a lyophilate comprising Compound 1.

4. Reconstitution to Give a Pharmaceutical Composition

The reconstitution procedure in a vial was as follows:

First, 2.1 mL of ethanol was added to the lyophilate comprising Compound 1, and the vial was mixed for at least 30 seconds to solubilize the drug product.

Second, 2.1 mL of WFI was added, and the vial was mixed for at least 30 seconds to give a pharmaceutical composition comprising Compound 1. In this example, the final concentration of Compound 1 is 10 mg/mL.

5. Dilution to Give a Pharmaceutical Formulation

The dilution procedure was as follows.

First, the subject's dose (mg) of Compound 1 was calculated based on the subject's body surface area using the Mosteller equation and assigned dose level. The final concentration of the pharmaceutical formulation is between 0.012-0.24 mg/mL of Compound 1 in a final volume of 500 mL. For subjects assigned to doses≤3.3 $mg/m^2$ and with BSA≤1.82 $m^2$ utilize a final volume for administration of 250 mL to ensure the concentration is maintained between 0.012-0.24 mg/mL of Compound 1.

Second, the volume (mL) of the pharmaceutical composition needed to prepare the subject's dose was determined.

Third, the volume of 0.9% sodium chloride or other suitable diluent needed was determined by subtracting the volume of the pharmaceutical composition needed from 500 mL (or 250 mL for doses≤3.3 $mg/m^2$ and with BSA≤1.82 $m^2$).

Fourth, the volume of the dilute determined above was injected into a sterile polyolefin (non-DEHP and non-PVC) or other suitable infusion container (500 mL capacity).

Fifth, volume the pharmaceutical composition determined above was injected into the infusion container to give a pharmaceutical formulation for intravenous administration to a subject.

EXAMPLE 4

Pharmaceutical Formulation Properties

Study Number 1

The purity and concentration of Compound 1 as measured by HPLC were determined during a 24 hour test period while the drug product was held in its diluted state in normal saline in a polyvinyl chloride (PVC) clinical containers over a range of concentrations in 500 mL bags. The parameters of the study were:

Compound 1 dose: 6 mg and 150 mg in 500 mL
Concentration range: 0.012-0.3 mg/mL Compound 1
Container size: 500 mL
Diluent: 0.9% normal saline, USP
Stability time points: 0, 4, 8, 24 hours
Storage condition: room temperature (15-25° C.)
Container composition: polyvinyl chloride
Light conditions: ambient light vs amber IV bag covers to limit UV exposure
Reconstitution: 80% (v/v) ethanol for reconstitution of the lyophilate, followed by dilution into normal saline. After dilution, all the diluted samples remained clear through 24 hours.

Assay results demonstrated no significant loss of recovery up to 8 hours under ambient light and up to 24 hours with an amber covered shroud protecting the container from light.

Impurity testing demonstrated greater impurities under ambient light with an increase in impurities observed over the course of the experiment (0-24 hours). HPLC data indicated materials are extracted from the PVC container which was most evident at the lower concentrations. An increase in impurities was observed as compared to testing normal saline and ethanol vehicle controls.

Overall, the chemical and physical testing suggest Compound 1 is stable at room temperature for up to 8 hours under ambient light, and up to 24 hours with use of an amber covered shroud protected from light, at a concentration range of 0.012-0.3 mg/mL when diluted in normal saline in PVC containers.

Study Number 2

The purity and concentration of Compound 1 as measured by HPLC were determined during a 5 hour test period while the drug product was held in polyvinyl chloride (PVC) and non-PVC, non-DEHP (polyolefin) clinical containers over a range of concentrations in 500 mL containers. Admixed containers were delivered with an Alaris infusion set by holding the infusion bag with diluted test article for 4 hours prior to a 1 hour infusion to assess in use stability over a total of 5 hours to mimic clinical practice. The parameters of the study were:

Compound 1 dose: 6 mg and 150 mg in 500 mL
Concentration range: 0.012-0.3 mg/mL Compound 1
Container size: 500 mL
Diluent: 0.9% normal saline, USP
Stability time points: 0 hours, 4 hours (pre-infusion), 5 hours (post-1 hour infusion)
Storage condition: room temperature (15-25° C.)
Container composition: polyvinyl chloride and non-PVC, non-DEHP (polyolefin)
Light conditions: ambient light vs amber IV bag covers to limit UV exposure
Reconstitution: 80% (v/v) ethanol for reconstitution of the lyophilate, followed by dilution into normal saline. After dilution, all the diluted samples remained clear through 5 hours.

Assay results demonstrate no significant loss of recovery up through 4 hour hold and 1 hour infusion with and without an amber covered shroud protecting the container from light and regardless of container composition.

Impurity testing demonstrated greater impurities under ambient light with an increase in impurities observed over the course of the experiment (4 hours and 1 hour post infusion compared to baseline).

Per Study Number 1, it is thought materials extracted from the PVC containers (extractables) may be evident as demonstrated in increased concentrations of certain impurities over time, which was only observed for the 0.012 mg/mL Compound 1 (lower concentration) studies. This was not observed in polyolefin containers.

Overall, the chemical and physical testing suggest Compound 1 is stable at room temperature for up to 4 hours followed by a 1 hour infusion with use of an amber covered shroud protected from light, in polyolefin containers, with low-sorb tubing at a concentration range of 0.012-0.3 mg/mL when diluted in normal saline.

Study Number 3

The purity and concentration of Compound 1 as measured by HPLC were determined during a 5 hour test period while the drug product was held in a non-DEHP (polyolefin) clinical containers over a range of concentrations in 500 mL containers. Admixed containers were delivered with an Alaris infusion set by holding the infusion bag with diluted test article for 4 hours prior to a 1 hour infusion to assess in use stability over a total of 5 hours to mimic clinical practice. The parameters of the study were:

Compound 1 dose: 6 mg and 120 mg in 500 mL
Concentration range: 0.012-0.24 mg/mL Compound 1
Container size: 500 mL
Diluent: 0.9% normal saline, USP
Stability time points: 0 hours, 4 hours (pre-infusion), 5 hours (post-1 hour infusion)
Storage condition: room temperature (15-25° C.)
Container composition: non-DEHP (polyolefin)
Light conditions: amber IV bag covers to limit UV exposure
Reconstitution: 50% (v/v) ethanol for reconstitution of the lyophilate, followed by dilution into normal saline. After dilution, all the diluted samples remained clear through 5 hours.

Assay results demonstrate no significant loss of recovery up through 4 hour hold and 1 hour infusion with both PVC and low sorbing infusion tubing sets.

Impurity testing demonstrated no impurities at any time point in all experiments.

Overall, the chemical and physical testing suggest Compound 1 is stable at room temperature for up to 4 hours followed by a 1 hour infusion with use of an amber covered shroud protected from light, in polyolefin containers, with either PVC or low-sorb tubing at a concentration range of 0.012-0.24 mg/mL when diluted in normal saline.

EXAMPLE 5

Process Optimization

Experiments were conducted to study the compounding and holding of pre-lyophilization solutions comprising Compound 1.

Vials of the compounded sterile filtered pre-lyophilization solutions were held at 17° C., 20° C., 22° C., and 25° C. In vials held at 17° C. at a concentration of 15 mg/mL (Exp #4), precipitation was barely visible at 1 h and clearly visible at 2 h. None of the other pre-lyophilization solutions showed precipitation at higher temperature or lower concentration at 24 h. A summary of the experimental results are provided in Table 7.

TABLE 7

| Experiment Number and Conditions | Procedure | Result |
|---|---|---|
| 1. Compounding of excipients of at 17° C. without any Compound 1 (i.e., placebo solution). | Dissolve PVP and histidine at 17° C. and titrate to pH 6.7. Add ethanol at 17° C. and t-butanol at 30° C. Cool mixture to 17° C. and monitor for precipitation. | No precipitation or difficulty of compounding was observed. 40° C. is suggested as the optimum temperature to warm the t-butanol |
| 2. Compounding of excipients and Compound 1 (15 mg/mL) at 25° C. using a single vessel | Dissolve PVP and histidine at 25° C. and titrate to pH 6.7. Add ethanol at 25° C. and t-butanol at 40° C. Bring mixture to 25° C. and dissolve Compound 1 at 15 mg/mL. | Dissolution time: >6.5 h (estimated at 9.5 h) |
| 3. Compounding of excipients and Compound 1 (15 mg/mL) in two vessels (separate aqueous and organic) | Dissolve PVP and histidine at 25° C. and titrate to pH 6.7. Attempt to dissolve Compound 1 in ethanol and t-butanol at 25° C. Take steps up to 30° C. and 35° C. if Compound 1 does not dissolve at lower temperature. Mix aqueous and | No advantage of organic dissolution; a substantial portion of the Compound 1 remains as solid even at 35° C. Dissolution time was reduced to 1.25 h, but that was seen as being primarily due to temperature at the time aqueous and organic |

TABLE 7-continued

| Experiment Number and Conditions | Procedure | Result |
|---|---|---|
| | organic portions and wait for complete dissolution. Temperature of the mixture is held at whatever temperature the organic phase was at the time of addition. | were combined, not due to the use of organic dissolution first. Dissolution time: 1.25 h. |
| 4. Compounding of excipients and Compound 1 (15 mg/mL) at 30° C. using a single vessel | Dissolve PVP and histidine at 25° C. and titrate to pH 6.7. Add ethanol at 25° C. and t-butanol at 40° C. Bring mixture to 30° C. and dissolve Compound 1 at 15 mg/mL. Sterile filter and hold 17° C., 20° C., 22° C., and 25° C. | Dissolution time: 5 h Precipitation post filtration was not observed for product held at 20° C., 22° C., or 25° C. Precipitation was observed in vial held at 17° C. at 1 h. |
| 5. Compounding of excipients and Compound 1 (12.5 mg/mL) at 30° C. using a single vessel | Dissolve PVP and histidine at 25° C. and titrate to pH 6.7. Add ethanol at 25° C. and t-butanol at 40° C. Bring mixture to 30° C. and dissolve Compound 1 at 12.5 mg/mL. Sterile filter and hold 17° C., 20° C., 22° C., and 25° C. | Dissolution time: 3.66 h No precipitation observed post filtration in vials stored at 17° C., 20° C., 22° C., or 25° C. for 24 h. |
| 6. Compounding ofexcipients and Compound 1 (10 mg/mL) at 30° C. using a single vessel | Dissolve PVP and histidine at 25° C. and titrate to pH 6.7. Add ethanol at 25° C. and t-butanol at 40° C. Bring mixture to 30° C. and dissolve Compound 1at 10 mg/mL. Sterile filter and hold 17° C., 20° C., 22° C., and 25° C. | Dissolution time: 1.75 h No precipitation observed post filtration in vials stored at 17° C., 20° C., 22° C., or 25° C. for 24 h. |

Based on these data, a compounding concentration of 10 mg/mL was selected for Compound 1. The critical process parameters are provided in Table 8.

TABLE 8

| Process Step* | Process Parameters and Set Points (for 10 mg/mL) | Comments |
|---|---|---|
| 1. Compound excipients and add t-butanol and ethanol | t-Butanol temperature: 40° C Solution temperature during compounding: room temperature (>17° C.) or higher. | Compounding of the excipients was accomplished at 17° C. It is important to liquify the t-butanol. 40° C. is recommend for liquification. Once the t-butanol is added to the vessel, 17° C. is sufficient to maintain a workable solution. |
| 2. Add Compound 1 and dissolve | Solution temperature and mixing time: 30° C. (1.75 h) or 25° C. (if 30° C. represents an engineering challenge for processing equipment). | Complete mixing should be verified visually. High shear mixing is not required, but the drugs substance particles should be mixed enough to maintain a uniform suspension until dissolution occurs. |

TABLE 8-continued

| Process Step* | Process Parameters and Set Points (for 10 mg/mL) | Comments |
|---|---|---|
| 3. Sterile filter | Filtration temperature: ≥17° C. | At 17° C., precipitation occurs within 1 h at 15 mg/mL. |
| 4. Hold prior to filling | Filtration temperature: ≥17° C. | 12.5 mg/mL and 10 mg/mL remain free of precipitation at that temperature for 24 h. |
| 5. Place vials in lyophilizer | Lyophilization loading temperature: 20° C. | A temperature of 20° C. will ensure that precipitation does not occur. |

It is to be understood that the foregoing described embodiments and exemplifications are not intended to be limiting in any respect to the scope of the disclosure, and that the claims presented herein are intended to encompass all embodiments and exemplifications whether or not explicitly presented herein All patents and publications cited herein are fully incorporated by reference in their entirety.

What is claimed is:

1. A lyophilate comprising(S)-isopropyl 2-((S)-2-acetamido-3-(1H-indol-3-yl)propanamido)-6-diazo-5-oxohexanoate, a stabilizing agent, and a buffering agent, wherein the (S)-isopropyl 2-((S)-2-acetamido-3-(1H-indol-3-yl)propanamido)-6-diazo-5-oxohexanoate/buffering agent weight ratio is about 6.5.

2. The lyophilate of claim 1, wherein the (S)-isopropyl 2-((S)-2-acetamido-3-(1H-indol-3-yl)propanamido)-6-diazo-5-oxohexanoate/stabilizing agent weight ratio is about 0.67.

3. The lyophilate of claim 1, wherein the stabilizing agent is polyvinylpyrrolidone.

4. The lyophilate of claim 1, wherein buffering agent is L-histidine.

5. The lyophilate of claim 1 comprising about 42 mg of (S)-isopropyl 2-((S) -2-acetamido-3-(1H-indol-3-yl)propanamido)-6-diazo-5-oxohexanoate.

6. The lyophilate of claim 3 comprising about 63 mg of polyvinylpyrrolidone.

7. A pharmaceutical composition comprising (S)-isopropyl 2-((S)-2-acetamido-3-(1H-indol-3-yl)propanamido)-6-diazo-5-oxohexanoate, a stabilizing agent, and a solvent comprising about 45% vol/vol to about 55% vol/vol ethanol and about 55% vol/vol to about 45% vol/vol water.

8. The pharmaceutical composition of claim 7, wherein the (S)-isopropyl 2-((S)-2-acetamido-3-(1H-indol-3-yl)propanamido)-6-diazo-5-oxohexanoate concentration is about 10 mg/mL.

9. A pharmaceutical formulation comprising the pharmaceutical composition of claim 7 and a diluent.

10. The pharmaceutical formulation of claim 9, wherein the (S)-isopropyl 2-((S)-2-acetamido-3-(1H-indol-3-yl)propanamido)-6-diazo-5-oxohexanoate concentration is about 0.012 to about 0.24 mg/mL.

11. A method for treating cancer in a subject in need thereof, the method comprising administering a therapeutically effective amount of the pharmaceutical formulation of claim 10 to the subject.

12. The method of claim 11, wherein the pharmaceutical formulation is administered intravenously to the subject.

13. A method of making the lyophilate of claim 1, the method comprising:

(i) dissolving (S)-isopropyl 2-((S)-2-acetamido-3-(1H-indol-3-yl)propanamido)-6-diazo-5-oxohexanoate in a mixture of a stabilizing agent, a buffering agent, t-butanol, ethanol, and water at a temperature of about 25° C. to about 35° C. to give a pre-lyophilization solution;

(ii) cooling the pre-lyophilization solution until it is frozen or partially frozen; and (iii) applying a vacuum to the frozen or partially frozen pre-lyophilization solution to give the lyophilate.

14. The method of claim 13, wherein the stabilizing agent comprises polyvinylpyrrolidone and the buffering agent comprises L-histidine.

15. The method of claim 13, wherein the concentration of (S)-isopropyl 2-((S)-2-acetamido-3-(1H-indol-3-yl)propanamido)-6-diazo-5-oxohexanoate in the pre-lyophilization solution is about 10 mg/mL.

16. A kit comprising the lyophilate of claim 1 packaged as single unit dose in a vial.

17. The method of claim 11, wherein the cancer is hepatocellular carcinoma, glioblastoma, lung cancer, breast cancer, head and neck cancer, prostate cancer, melanoma, or colorectal cancer.

* * * * *